(12) United States Patent
Vagle et al.

(10) Patent No.: US 9,012,225 B2
(45) Date of Patent: Apr. 21, 2015

(54) LIPOPHILIC POLYNUCLEOTIDE CONJUGATES

(75) Inventors: Kurt Vagle, Longmont, CO (US); William S. Marshall, Boulder, CO (US)

(73) Assignee: miRagen Therapeutics, Boulder, CO (US)

( * ) Notice: Subject to any disclaimer, the term of this patent is extended or adjusted under 35 U.S.C. 154(b) by 127 days.

(21) Appl. No.: 13/319,270

(22) PCT Filed: May 5, 2010

(86) PCT No.: PCT/US2010/033729
§ 371 (c)(1), (2), (4) Date: Feb. 1, 2012

(87) PCT Pub. No.: WO2010/129672
PCT Pub. Date: Nov. 11, 2010

(65) Prior Publication Data
US 2012/0128761 A1 May 24, 2012

Related U.S. Application Data

(60) Provisional application No. 61/175,690, filed on May 5, 2009.

(51) Int. Cl.
| | | |
|---|---|---|
| A61K 9/127 | (2006.01) | |
| A61K 31/7105 | (2006.01) | |
| C07H 21/02 | (2006.01) | |
| C07H 21/04 | (2006.01) | |
| C07J 41/00 | (2006.01) | |
| C07J 43/00 | (2006.01) | |
| C07J 51/00 | (2006.01) | |
| C12N 15/87 | (2006.01) | |
| C12N 15/11 | (2006.01) | |
| C12N 15/113 | (2010.01) | |
| A61K 48/00 | (2006.01) | |

(52) U.S. Cl.
CPC ............ *C07J 41/0055* (2013.01); *C07J 43/003* (2013.01); *C07J 51/00* (2013.01); *C12N 15/87* (2013.01); *C12N 15/111* (2013.01); *C12N 15/113* (2013.01); *A61K 48/0033* (2013.01); *C12N 2310/113* (2013.01); *C12N 2310/315* (2013.01); *C12N 2310/3515* (2013.01)

(58) Field of Classification Search
None
See application file for complete search history.

(56) References Cited

U.S. PATENT DOCUMENTS

| 2003/0134420 A1 | 7/2003 | Lollo et al. |
| 2005/0107325 A1 | 5/2005 | Manoharan et al. |
| 2005/0130911 A1 | 6/2005 | Uhlmann et al. |
| 2008/0199960 A1 | 8/2008 | Juliano et al. |

FOREIGN PATENT DOCUMENTS

| WO | WO 2004/065601 | 8/2004 |
| WO | WO 2006/031461 | 3/2006 |
| WO | WO 2007/086881 | 8/2007 |

OTHER PUBLICATIONS

Lehmann, T. J. et al., "Synthesis and properties of bile acid phosphoramidites 5'-tethered to antisense oligodeoxynucleotides against HCV," Bioorganic & Medicinal Chemistry, 9(7):1827-1835 (2001).
Godeau, G. et al., "Lipid-conjugated oligonucleotides via 'click chemistry' efficiently inhibit hepatitis C virus translation," Journal of Medicinal Chemistry, 51(15):4374-4376 (2008).
Matysiak, S. et al., "Acetal oligonucleotide conjugates in antisense strategy," Nucleosides & Nucleotides, 16(5&6):855-861 (1997).
Monaco, V. et al., "Synthesis and biological evaluation of modified DNA fragments for the study of nucleotide excision repair in *E. coli*.," Nucleosides & Nucleotides, 18(6&7):1339-1341 (1999).
Maru, N. et al., "Successive fusion of vesicles aggregated by DNA duplex formation in the presence of Triton X100," Chemistry Letters, 37(3):340-341 (2008).
Maru, N. et al., "Assembling liposomes by means of an oligonucleotide tagged with a lipophilic unit," Nucleic Acids Symposium Series, 48:95-96 (2004).
Supplementary European Search Report for European Application No. 10772765, mailed Feb. 5, 2013, 10 pages.
Young, "International Search Report and Written Opinion," 11 pages, International Application No. PCT/US2010/033729, U.S. Patent Office, Alexandria, VA, mailed Sep. 17, 2010.
Office Action, Japanese Application Serial No. 2012-509948, issued Aug. 22, 2014, 5 pages.

*Primary Examiner* — Janet Epps-Smith
(74) *Attorney, Agent, or Firm* — Cooley LLP

(57) ABSTRACT

Disclosed are lipophilic polynucleotide conjugates including polynucleotide-cholesterol conjugates and methods of delivering therapeutic polynucleotides to a mammalian cell or patient in need of treatment using said conjugates. The disclosure further provides methods of synthesizing the lipophilic polynucleotide conjugates. The conjugates are designed to mimic or target cellular miRNAs. The lipophilic moiety, such as cholesterol or cholesterol derivative, is spaced from the polynucleotide by a substantially linear hydrocarbon group. Due to an absence of significantly polar groups and/or exchangeable protons in the vicinity of the lipophilic moiety, the interaction between the lipophilic moiety and cell membranes is enhanced to provide for efficient entry into cells.

45 Claims, 6 Drawing Sheets

LIPOPHILIC POLYNUCLEOTIDE CONJUGATES

CROSS-REFERENCE TO RELATED APPLICATIONS

This application is a national stage application of International Application No. PCT/US2010/033729, filed May 5, 2010, which claims the benefit of priority of U.S. Provisional Application No. 61/175,690 filed May 5, 2009, both of which are herein incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_014_00WO_SeqList_ST25.txt, date recorded: May 4, 2010, file size 10 kilobytes)

FIELD OF THE INVENTION

The present invention relates to lipophilic conjugates of nucleic acid for the delivery of polynucleotides to cells for therapeutic, research and/or diagnostic purposes. The invention relates in certain embodiments to the delivery of polynucleotides that target endogenous microRNA function.

BACKGROUND

Oligonucleotide therapeutic strategies rely on delivering the hydrophillic, highly charged and anionic nucleic acid molecule into the cytoplasm by crossing the hydrophobic phospholipid bilayer that constitutes the cell membrane. Hydrophobic conjugates of oligonucleotides have been investigated for their ability to enhance cellular uptake. For example, cholesterol conjugates may be capable of binding to lipoproteins, and more specifically IDL and LDL particles. The particles contain ApoE and ApoB-100 lipoproteins, which target LDL cell surface receptors and, therefore, can be internalized via lipoprotein mediated endocytosis. These receptors are found mainly in the liver, but also in adipose tissue, heart and skeletal muscle. Additionally, pendant lipophillic groups may aid in "anchoring" their conjugates to the cell membrane by intercalating into the phospholipid bilayer and therefore aiding passive internalization of the oligonucleotide.

Such lipophilic molecules or substitutents must be formulated with, or attached to, the polynucleotide so as to preserve the functional and structural integrity of the polynucleotide for its desired therapeutic action. For example, therapeutic polynucleotides may function through interactions with large and/or intricate ribonucleoprotein (RNP) complex(es), and/or may target RNA components of these complexes. Lipophilic modifications should therefore not impair the accessibility of the polynucleotide for interactions with cellular factors and molecular targets.

MicroRNAs (miRs) have been implicated in a number of biological processes including regulation of developmental timing, apoptosis, fat metabolism, and hematopoietic cell differentiation among others, and therefore represent a relatively new class of therapeutic targets. miRs are small, non-protein coding RNAs of about 18 to about 25 nucleotides in length, and act as repressors of target mRNAs by promoting their degradation, when their sequences are perfectly complementary, or by inhibiting translation, when their sequences contain mismatches. The mature miRNA strand is incorporated into the RNA-induced silencing complex (RISC), where it associates with its target RNAs by base-pair complementarity.

Compositions and methods for efficiently delivering therapeutic polynucleotides, including miRs and miR inhibitors, to cells without substantially or significantly impairing interactions with the molecular target(s) are needed.

SUMMARY OF THE INVENTION

The present invention provides lipophilic polynucleotide conjugates, and methods of delivering therapeutic polynucleotides to a mammalian cell or a mammalian patient in need of treatment. The invention further provides methods of synthesizing the lipophilic polynucleotide conjugates. In accordance with the invention, the conjugates include conjugates of cholesterol and polynucleotides, designed to mimic or target cellular miRNAs. The lipophilic moiety, such as cholesterol or cholesterol derivative, is spaced from the polynucleotide by a hydrocarbon group. Due to an absence of significantly polar groups and/or exchangeable protons in the vicinity of the lipophilic moiety, the invention enhances the interaction between the lipophilic moiety and cell membranes to provide for efficient entry into cells. The conjugate does not substantially or significantly disrupt the ability of the polynucleotide to deliver its therapeutic effect.

In one aspect, the invention provides a lipophilic polynucleotide conjugate as well as pharmaceutical compositions and formulations comprising the same. In accordance with this aspect, the lipophilic moiety may be a cholesterol or similar lipophilic structure as described herein, or other group that associates with membrane phospholipids. The polynucleotide may be DNA- or RNA-based, and/or may embody one or more nucleic acid modifications, for example, such as a modified polynucleotide backbone or one or more modified nucleoside units. For example, the modified backbone may be a full or partial phosphorothioate modified backbone. The sequence of the polynucleotide may be designed so as to mimic a miRNA or target a miRNA by antisense inhibition, for example. The polynucleotide and lipophilic moiety are spaced by, and conjugated through, a substantially linear hydrocarbon moiety (e.g., linker). The hydrocarbon linker may be conjugated to the 5' and/or 3' end of the polynucleotide, for example.

The conjugate of the invention has an absence of significantly polar groups, such as groups having an exchangeable proton, within the vicinity of the lipophilic moiety. For example, the hydrocarbon may be conjugated to the lipophilic moiety (e.g., cholesterol) through a relatively non-polar group such as an ether or thioether linkage, and the hydrophobic linker may comprise from about 3 to about 15 carbon atoms. The absence of a significantly polar group, e.g., having an exchangeable proton, in the vicinity of the lipophilic moiety allows the moiety to better intercalate with membrane phospholipids upon delivery to a cell or patient.

In a second aspect, the invention provides a method for delivering polynucleotides to a mammalian cell, and methods for treating or preventing the progression of a condition in a mammalian patient. In this aspect, the invention comprises administering the polynucleotide as a conjugate with cholesterol or other lipophilic moiety as described herein. The polynucleotide may be a miRNA or a miRNA inhibitor (e.g., having a nucleotide sequence designed to inhibit expression or activity of a miRNA). In such embodiments, the patient has a condition associated with RNA expression, such as miRNA expression. Such conditions include, for example, cardiac hypertrophy, myocardial infarction, heart failure (e.g., congestive heart failure), vascular damage, restenosis, and/or pathologic cardiac fibrosis, among others.

In a third aspect, the invention provides a method for synthesizing the polynucleotide conjugates. The invention provides methods of synthesizing polynucleotides having lipophilic moieties conjugated at the 5' and/or 3' end, or along the polynucleotide backbone, through a hydrocarbon moiety or linker. In certain embodiments where the lipophilic moiety is an alcohol, such as a sterol, the lipophilic moiety is etherized with a hydrocarbon having a suitable terminal functional group. This ether-linked intermediate may be further reacted to prepare suitable reagents compatible with solid phase nucleic acid synthesis. For example, the ether-linked intermediate may be further reacted to prepare a terminal phosphoramidite (e.g., through an ether linkage) for converting to a phosphate ester (e.g., coupling to a nucleotide 5' hydroxyl during polynucleotide synthesis). Alternatively, or in addition, the ether-linked intermediate may be further reacted to prepare a suitable terminal group for coupling (e.g. via amidation) to a suitable support for nucleic acid synthesis.

Alternatively, the invention provides a method for synthesizing cholesterol conjugates with polynucleotides, after synthesis of the polynucleotide is complete, using for example, carbonyl addition-elimination/reductive amination, amidation, maleimide-thiol coupling, aqueous Diels-Alder and "Click" chemistries.

DETAILED DESCRIPTION OF THE INVENTION

Figure 1:
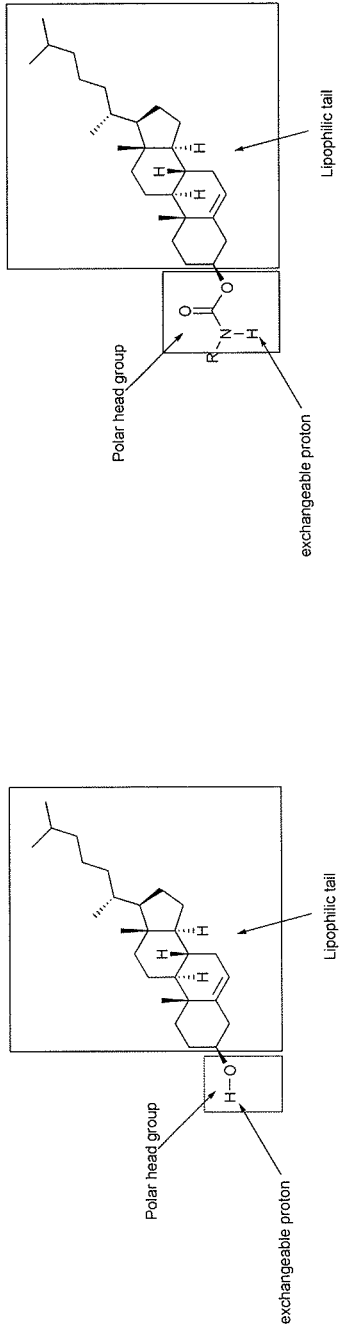
FIG. 1 illustrates an exemplary lipophilic (cholesterol) conjugate of the invention as compared to conventional conjugates. In accordance with the invention, polar groups such as those having exchangeable protons are removed from the vicinity of the cholestene ring structure.
Figure 1:
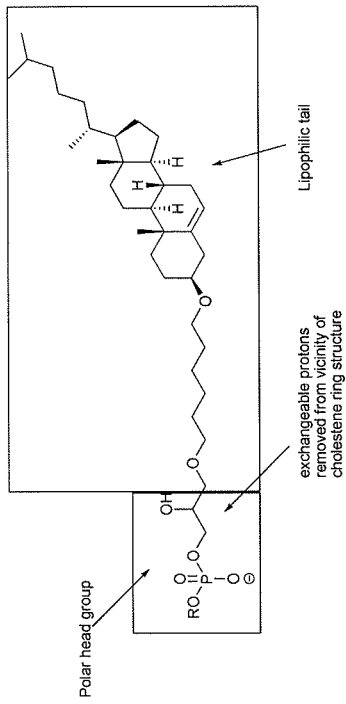

Active and/or passive cellular transport mechanisms may benefit from pendant lipophillic groups, including those that are native to the phospholipid bilayer and which should efficiently pack in the bilayer. Thus, the invention provides conjugates that contain a sufficiently hydrophobic linker to efficiently pack into a phospholipid bilayer, to thereby enhance the affinity of the polynucleotide conjugates for cell membranes, or alternatively liposomes or micelles that may act as delivery vehicles. Oligonucleotide-cholesterol type conjugates have generally employed cholesteryl carbamate linkages that result in a polar group containing an exchangeable proton immediately adjacent to the steroid ring structure. These conjugates do not have optimized lipophillic properties and the polar linkage point may impede efficient phospholipid bilayer packing.

The present invention provides lipophilic polynucleotide conjugates, and methods of delivering therapeutic polynucleotides to a mammalian cell or a mammalian patient in need of treatment. The invention further provides methods of synthesizing the lipophilic polynucleotide conjugates. In accordance with the invention, the conjugates may be designed to target cellular RNAs, including miRNAs. For example, the conjugates may target cellular miRNAs by antisense inhibition, or may be designed to mimic a miRNA. The lipophilic moiety, such as cholesterol or other lipophilic group, is spaced from the polynucleotide by a hydrocarbon linker. Due to an absence of significantly polar groups and/or exchangeable protons in the vicinity of the lipophilic moiety, the invention promotes interaction of the lipophilic moiety with membrane phospholipids, thereby providing efficient entry into cells. The conjugate does not substantially or significantly disrupt the ability of the polynucleotide to deliver its therapeutic effect.

Lipophilic Moiety and Hydrocarbon Spacer

The lipophilic moiety is a fat soluble moiety capable of intercalating with a phospholipid bi-layer, such as a cell membrane, or delivery vehicle such as a liposome or micelle as disclosed herein. The lipophilic moiety may be conjugated to the hydrocarbon spacer (described below) through an ether or thioether linkage. Exemplary lipophilic moieties include cholesterol and cholesterol derivatives (including cholestenes, cholestanes, and cholestadienes), bile acids (such as cholic acid, deoxycholic acid and dehydrocholic acid), sterols, steroids, or other fat soluble alcohol or thiol. In certain embodiments, the lipophilic moiety is cholesterol or a cholesterol derivative, or cholic acid or cholic acid derivative as described in U.S. Pat. No. 7,202,227, which is hereby incorporated by reference. Such derivatives include C1-C4 alkyl (e.g., methyl) substituted cholesterol or cholic acid structures.

For example, in certain embodiments, the cholesterol or derivative may have the following structure:

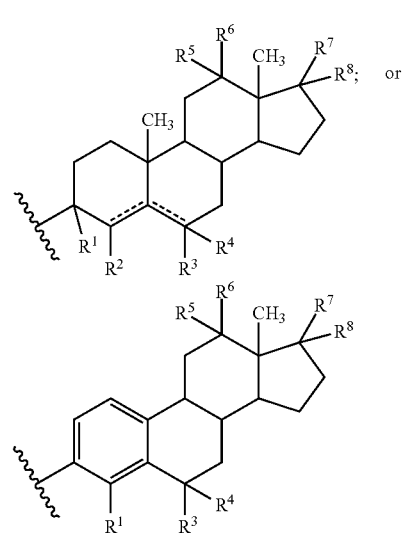

In such structures, each of $R^1$ through $R^8$ is a substantially non-polar group. For example, each of $R^1$ through $R^8$ may be independently selected from hydrogen, alkyl (e.g., C1-C6 alkyl), substituted alkyl, alkoxy (e.g., C1-C6 alkoxy) which may be substituted, and alkoxyalkyl which may be substituted. In certain embodiments, the lipophilic moiety has the following formula, where R is alkyl (e.g., C1-C10 alkyl):

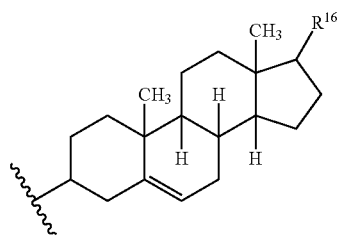

A hydrocarbon moiety or spacer separates the lipophilic moiety (described above) from non-lipophilic, e.g., polar, groups, so as to allow the lipophilic moiety to better interact with, inter alia, membrane phospholipids upon delivery to a patient or upon contact with mammalian cells. Thus, the conjugate generally does not have exchangeable protons or other polar groups (e.g., hydroxyl or amide) within the vicinity of the lipophilic moiety. Generally, there are no significantly polar groups and exchangeable protons within about 3 to about 15 atoms from the lipophilic moiety. In certain embodiments, the first significantly polar group or exchangeable proton is at least 6, 7, 8 or 9 atoms from the lipophilic moiety.

The hydrocarbon spacer may be conjugated to the lipophilic moiety through a relatively non-polar bond, such as an ether or thioether linkage. For example, where the lipophilic moiety is cholesterol or other sterol, the hydrocarbon spacer may be ether-linked with the sterol hydroxyl group.

In certain embodiments, the hydrocarbon spacer comprises a C2 to C15 saturated or unsaturated hydrocarbon chain (e.g., alkylene or alkenylene), and may be substituted by relatively non-polar substituents. Such substituents generally do not contain exchangeable protons or polar groups within the vicinity of the lipophilic moiety as described. For example, the substituents may be independently selected from alkyl (e.g., C1-C6 alkyl), alkoxy (e.g., C1-C6 alkoxy), and alkoxyalkyl. Where polar substituents are present, they are spaced at least about 6, 7, 8, or 9 atoms from the lipophilic moiety. Where unsaturated, the hydrocarbon spacer may comprise 1, 2, or 3 double bonds. In certain embodiments, the hydrocarbon spacer comprises a C2 to C10, or a C4 to C8 saturated hydrocarbon chain. For example, the hydrocarbon spacer may comprise a C4 or C6 saturated hydrocarbon.

In certain embodiments, the hydrocarbon chain contains one or more heteroatoms (e.g., from 1 to 5), such as heteroatoms independently selected from O, S, and/or N. In certain other embodiments, the hydrocarbon chain does not have any heteroatoms, except in some embodiments as desired or resulting from the attachment of the polynucleotide to the terminus by an ether or thioether linkage.

The hydrocarbon spacer is conjugated on the end opposite the lipophilic moiety to the polynucleotide, e.g., through a nucleotide 5' or 3' position, or at other location along the polynucleotide backbone. The hydrocarbon spacer may be conjugated to the polynucleotide, e.g., to the nucleotide 5' or 3' position, via any suitable functional group, including phosphodiester, ether, thioether, ester, thioester, or amide.

An exemplary conjugate of the invention may have a structure selected from structures (I), (II), and (III), respectively, below:

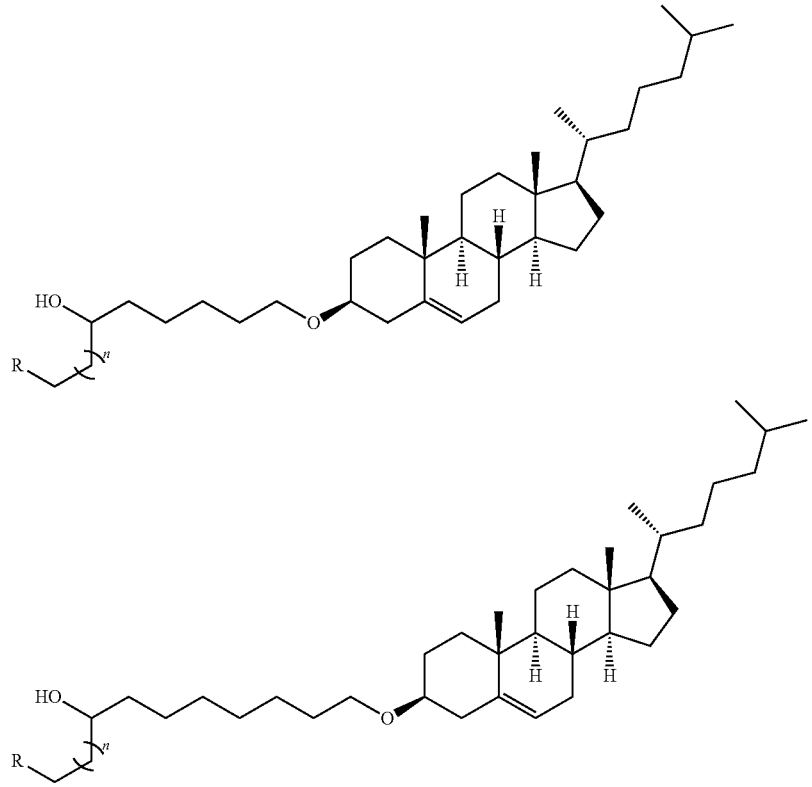

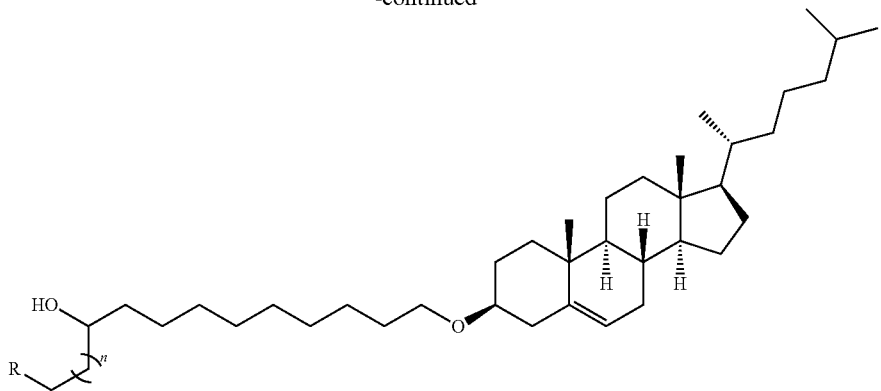
where n is 1 or 2, and where R may be a nucleotide or polynucleotide linked through the 3' or 5' position, optionally through a linking group.
Additional exemplary conjugates include structures (IV)-(VI), where R and R' are each H or phosphate polynucleotide, and structures VII-IX, where R and R' are each H, OH, or a phosphate polynucleotide.
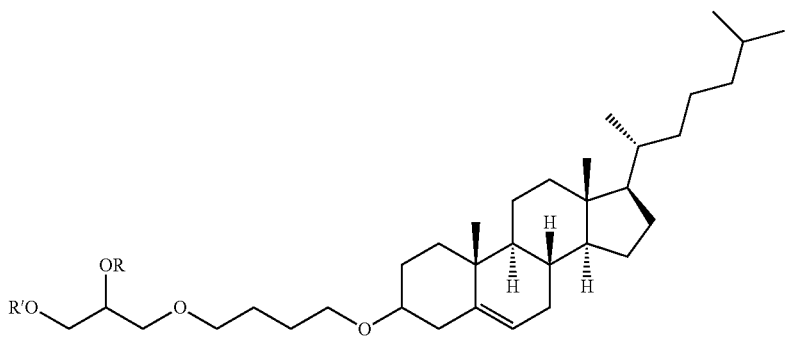
(IV)
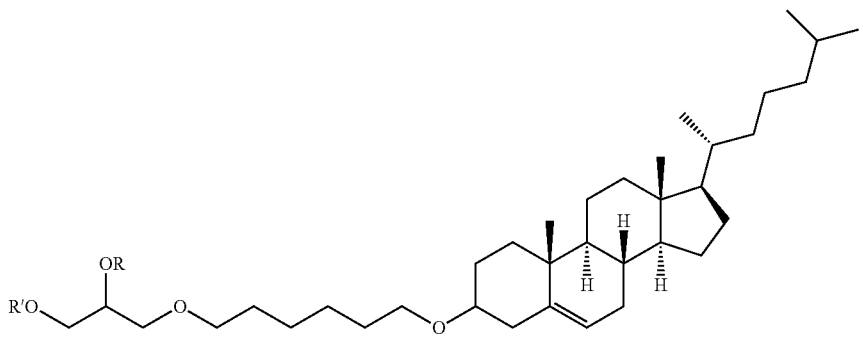
(V)
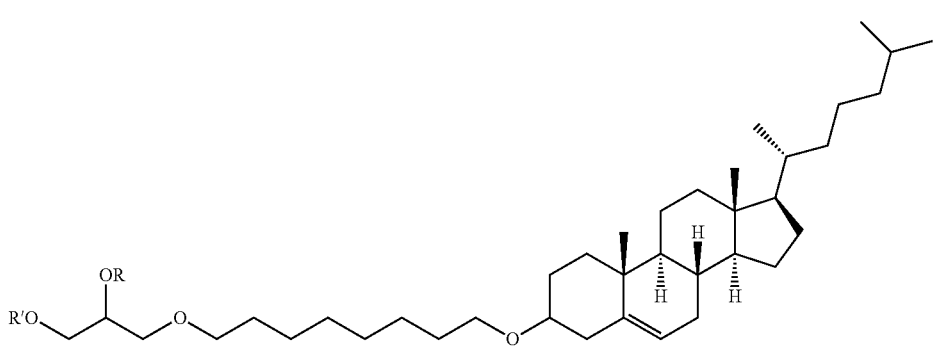
(VI)

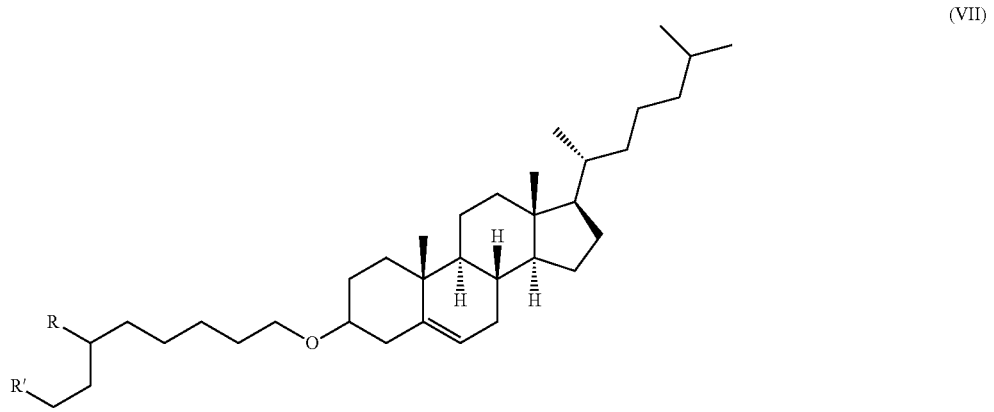
(VII)
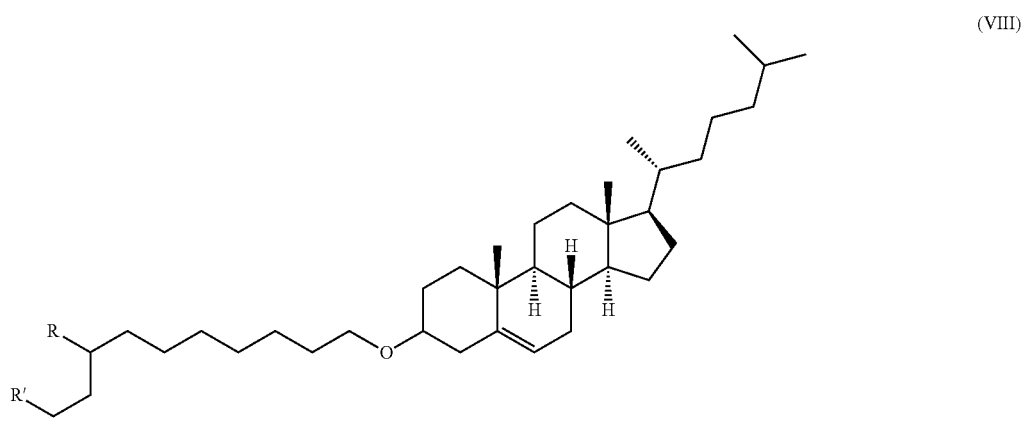
(VIII)
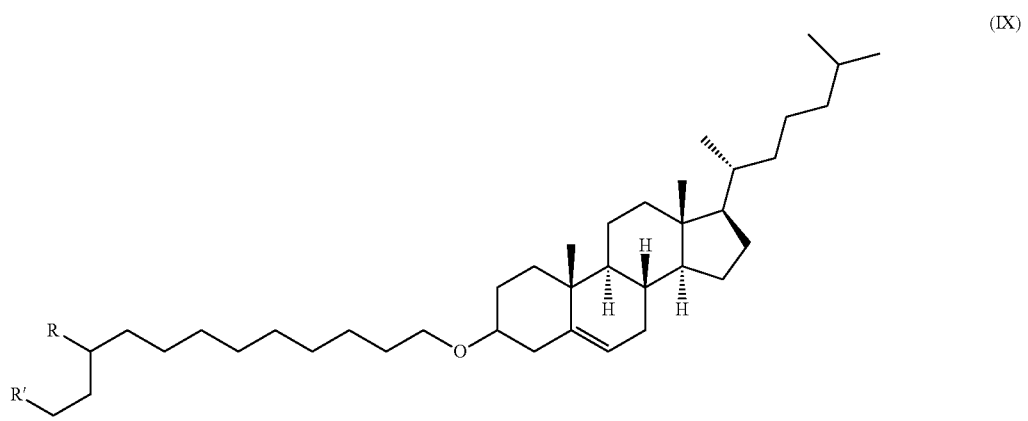
(IX)

In certain embodiments, the conjugate is a 5' conjugate having one of the following structures, where R is the polynucleotide chain:
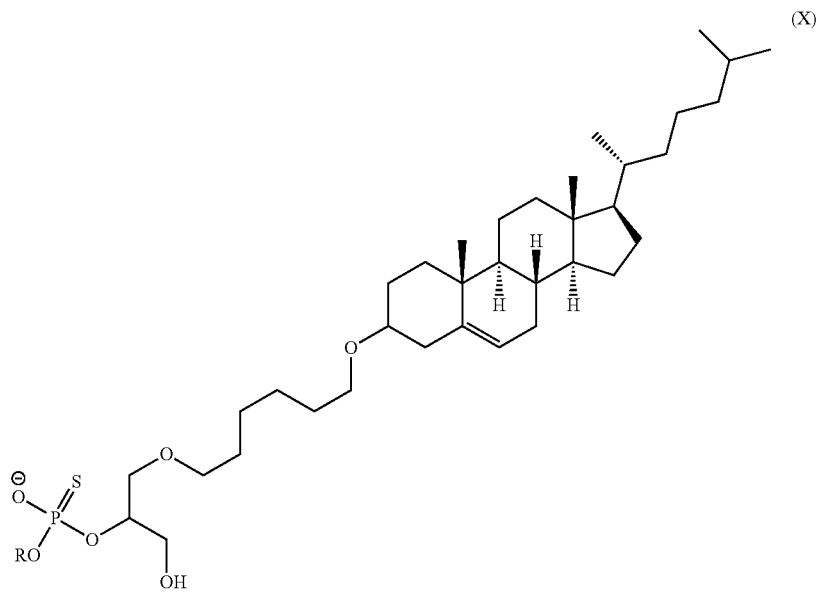
(X)
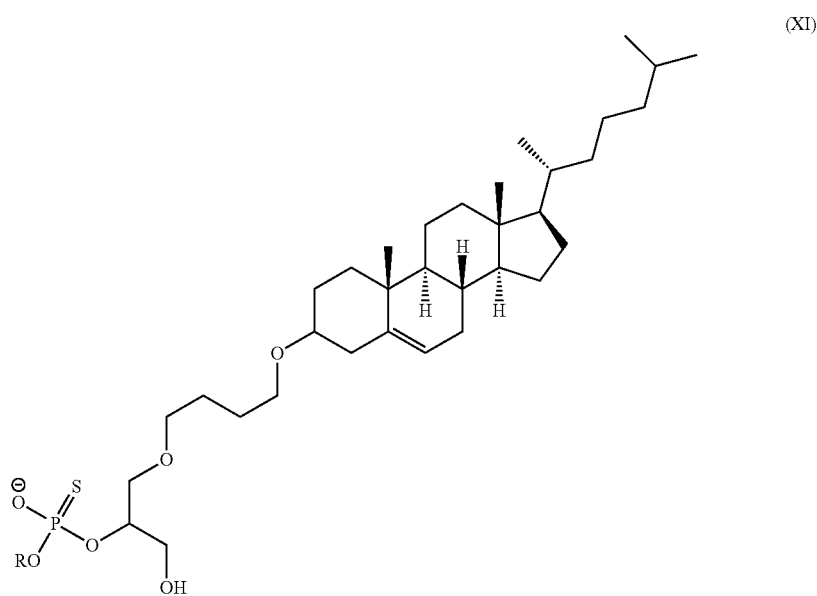
(XI)

In certain embodiments, the conjugate is a 3' conjugate having one of the following structures where R is the polynucleotide chain:

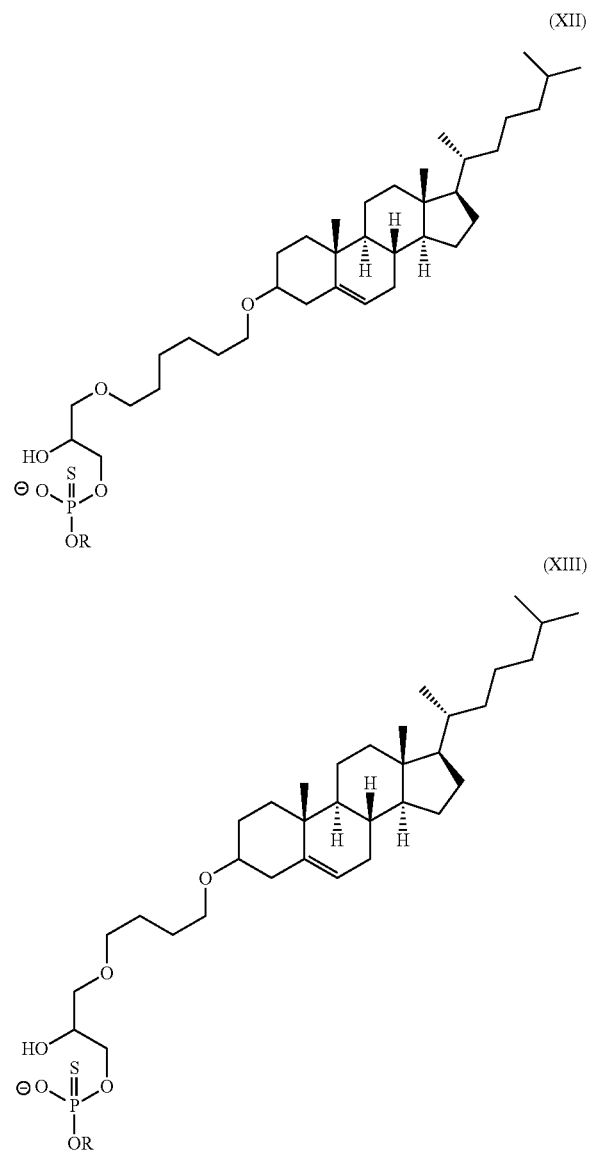

Polynucleotides

The compound, compositions and methods of the invention may employ various polynucleotides (including oligonucleotides) and derivatives thereof. The polynucleotide may be DNA- or RNA-based, and/or may embody one or more nucleic acid modifications, for example, such as a modified polynucleotide backbone or one or more modified nucleoside units. The polynucleotide or derivative may have one or more single stranded and/or one or more double stranded regions. The polynucleotide may be a an antisense oligonucleotide, short interfering RNA (siRNA), double stranded RNA (dsRNA), single stranded RNA (ssRNA), microRNA (miRNA), short hairpin RNA (shRNA), or ribozyme.

In certain embodiments, the compound, composition, or method employs a conjugated miRNA inhibitor (e.g., antisense inhibitor). Such inhibitors are described for example, in WO 2008/016924, WO 2009/062169, WO 2009/058818, WO 2009/018492, WO 2009/018493, WO 2009/012468, and WO 2007/070483, which are hereby incorporated by reference in their entireties.

Thus, the polynucleotide may be an antisense oligonucleotide. In some embodiments, the antisense oligonucleotide contains at least one chemical modification (e.g. sugar or backbone modification). For instance, antisense oligonucleotide may comprise one or more modified nucleotides, such as 2'-O-methyl-sugar modifications. In some embodiments, antisense oligonucleotides comprise only modified nucleotides. In certain embodiments, antisense oligonucleotides may also comprise one or more phosphorothioate linkages resulting in a partial or full phosphorothioate backbone. Antisense oligonucleotides suitable for inhibiting miRNAs may be about 5 to about 50 nucleotides in length, such as about 10 to about 30 nucleotides in length, or about 20 to about 25 nucleotides in length. In certain embodiments, antisense oligonucleotides are about 8 to about 18 nucleotides in length, and in other embodiments about 12 to about 16 nucleotides in length. The antisense oligonucleotide may comprise a sequence that is at least about 75%, 80%, 85%, 90%, 95%, 96%, 97%, 98%, or 99% complementary to a mature miRNA sequence (see Table 1 below). In other embodiments, the antisense oligonucleotides comprise a sequence that is 100% complementary to the mature miRNA sequence. As used herein "complementary" or "base pair" includes or refers only to classic Watson-Crick nucleotide base-pairing. In one embodiment, the antisense oligonucleotide is an antagomir. An "antagomir" is a single-stranded, optionally chemically-modified, ribonucleotide that is at least partially complementary to a miRNA sequence.

In certain embodiments, the polynucleotide has a sequence designed to mimic a cellular miRNA, such as a miRNA listed in Table 1. The polynucleotide in these embodiments may also comprise one or more modified nucleotides, such as 2'-O-methyl-sugar modifications, and one or more phosphorothioate linkages. Polynucleotides suitable for mimicking miRNAs may be about 15 to about 50 nucleotides in length, such as about 18 to about 30 nucleotides in length, or about 20 to about 25 nucleotides in length. The synthetic miRNA may comprise a sequence that is at least about 75%, 80%, 85%, 90%, 95%, 96%, 97%, 98%, or 99% identical to a mature miRNA sequence (see Table 1 below). In other embodiments, the polynucleotide comprises a sequence that is 100% identical to the mature miRNA sequence.

The polynucleotide may be composed of predominately ribonucleotide units or predominately deoxyribonucleotide units, and may have one or more chemical modification(s). For instance, the polynucleotides may be comprised of one or more "conformationally constrained" or bicyclic sugar nucleoside modifications (BSN) that confer enhanced thermal stability to complexes formed between the oligonucleotide containing BSN and their complementary microRNA target strand. In certain embodiments, the polynucleotide includes, for example, from about 1 to 10 locked nucleic acids. "Locked nucleic acids" (LNAs) contain the 2'-O, 4'-C-methylene ribonucleoside wherein the ribose sugar moiety is in a "locked" conformation. Alternatively or in addition, the polynucleotide may comprise peptide nucleic acids (PNAs), which contain a peptide-based backbone rather than a sugar-phosphate backbone. In these or other embodiments, the polynucleotide contains one or more sugar modifications and/or one or more backbone modifications. Exemplary sugar modifications include 2' and 4' modifications, such as 2'-O-alkyl (e.g. 2'-O-methyl, 2'-O-methoxyethyl), 2'-fluoro, and 4' thio modifications. Exemplary backbone modifications include phosphorothioate, morpholino, or phosphonocarboxylate linkages (see, for example, U.S. Pat. Nos. 6,693,187 and 7,067,641, which are herein incorporated by reference in their entireties).

In some embodiments, the polynucleotide is a 2'-O-methoxyethyl gapmer. A "gapmer" contains 2'-O-methoxy ethyl-modified ribonucleotides on both 5' and 3' ends with at least ten deoxyribonucleotides in the center. These "gapmers" are capable of triggering RNase-independent degradation mechanisms of RNA targets.

Other modifications of polynucleotides, for example, to enhance stability and/or improve antisense efficacy, are known, and may be employed in connection with the invention. Exemplary modifications are described in U.S. Pat. No. 6,838,283, which is hereby incorporated by reference in its entirety.

The polynucleotide may have a nucleotide sequence designed to mimic or target a miRNA, such as a miRNA listed in Table 1 below. In certain embodiments, the polynucleotide designed to inhibit a miRNA may have a sequence containing from 1 to 5 (e.g., 2, 3, or 4) mismatches relative to the fully complementary miRNA sequence (shown in Table 1 below). In other embodiments, the polynucleotide designed to mimic a miRNA may have a sequence containing from 1 to 5 (e.g., 2, 3, or 4) nucleotide substitutions relative to the mature miRNA sequence (shown in Table 1 below). Such antisense and sense sequences may be incorporated into shRNAs or other RNA structures containing stem and loop portions, for example. Such sequences are useful for, among other things, mimicking or targeting miRNA function for treatment or amelioration of cardiac hypertrophy, myocardial infarction, heart failure (e.g., congestive heart failure), vascular damage, and/or pathologic cardiac fibrosis, among others. Exemplary miRNA therapeutic utilities are disclosed in the US and PCT patent references listed in Table 1 below, each of which is hereby incorporated by reference in its entirety.

TABLE 1

| miRNA | miRNA Sequence | SEQ ID NO: | Reference |
|---|---|---|---|
| 1 | UGGAAUGUAAAGAAGUAUGUAU | 1 | WO 2009/012468 |
| 100 | AACCCGUAGAUCCGAACUUGUG | 2 | WO 2009/012468 |
| 10b | UACCCUGUAGAACCGAAUUUGUG | 3 | WO 2009/012468 |
| 125b | UCCCUGAGACCCUAACUUGUGA | 4 | WO 2009/012468 |
| 128 | UCACAGUGAACCGGUCUCUUU | 5 | WO 2007/070483 |
| 133a | UUUGGUCCCCUUCAACCAGCUG | 6 | WO 2009/012468 |
| 133b | UUUGGUCCCCUUCAACCAGCUA | 7 | WO 2009/012468 |
| 139 | UCUACAGUGCACGUGUCUCCAG | 8 | WO 2009/012468 |
| 143 | UGAGAUGAAGCACUGUAGCUC | 9 | WO 2007/070483 |
| 145 | GUCCAGUUUUCCCAGGAAUCCCU | 10 | WO 2007/070483 |
| 150 | UCUCCCAACCCUUGUACCAGUG | 11 | WO 2009/012468 |
| 15a | UAGCAGCACAUAAUGGUUUGUG | 12 | WO 2009/062169 |
| 15b | UAGCAGCACAUCAUGGUUUACA | 13 | WO 2009/062169 |
| 16 | UAGCAGCACGUAAAUAUUGGCG | 14 | WO 2009/062169 |
| 181b | AACAUUCAUUGCUGUCGGUGGGU | 15 | WO 2009/012468 |
| 195 | UAGCAGCACAGAAAUAUUGGC | 16 | WO 2009/012468 |

TABLE 1-continued

| miRNA | miRNA Sequence | SEQ ID NO: | Reference |
|---|---|---|---|
| 197 | UUCACCACCUUCUCCACCCAGC | 17 | WO 2009/012468 |
| 199a | CCCAGUGUUCAGACUACCUGUUC | 18 | WO 2009/012468 |
| 199b | miR-199b-5p CCCAGUGUUUAGACUAUCUGUUC | 19 | US 61/047,005 |
|  | miR-199b-3p ACAGUAGUCUGCACAUUGGUUA | 20 | |
| 206 | UGGAAUGUAAGGAAGUGUGUGG | 21 | WO 2007/070483 |
| 208a | AUAAGACGAGCAAAAAGCUUGU | 22 | WO 2008/016924 |
| 208b | AUAAGACGAACAAAAGGUUUGU | 23 | WO 2009/018492 |
| 20a | UAAAGUGCUUAUAGUGCAGGUAG | 24 | US 60/950,565 |
| 21 | UAGCUUAUCAGACUGAUGUUGA | 25 | WO 2009/058818 |
| 214 | ACAGCAGGCACAGACAGGCAGU | 26 | US 61/047,005 |
| 22 | AAGCUGCCAGUUGAAGAACUGU | 27 | WO 2009/012468 |
| 221 | AGCUACAUUGUCUGCUGGGUUUC | 28 | WO 2009/012468 |
| 222 | AGCUACAUCUGGCUACUGGGU | 29 | WO 2009/012468 |
| 224 | CAAGUCACUAGUGGUUCCGUU | 30 | WO 2009/012468 |
| 23a | AUCACAUUGCCAGGGAUUUCC | 31 | WO 2009/012468 |
| 26a | UUCAAGUAAUCCAGGAUAGGCU | 32 | WO 2007/070483 |
| 26b | UUCAAGUAAUUCAGGAUAGGU | 33 | WO 2009/012468 |
| 28 | AAGGAGCUCACAGUCUAUUGAG | 34 | WO 2009/012468 |
| 29a | UAGCACCAUCUGAAAUCGGUUA | 35 | WO 2009/018493 |
| 29b | UAGCACCAUUUGAAAUCAGUGUU | 36 | WO 2009/018493 |
| 29c | UAGCACCAUUUGAAAUCGGUUA | 37 | WO 2009/018493 |
| 30a | UGUAAACAUCCUCGACUGGAAG | 38 | PCT/US2010/031147 |
| 30b | UGUAAACAUCCUACACUCAGCU | 39 | PCT/US2010/031147 |
| 30c | UGUAAACAUCCUACACUCUCAGC | 40 | WO 2009/012468 |
| 30d | UGUAAACAUCCCCGACUGGAAG | 41 | PCT/US2010/031147 |
| 30e | UGUAAACAUCCUUGACUGGAAG | 42 | PCT/US2010/031147 |
| 342-3p | UCUCACACAGAAAUCGCACCCGU | 43 | WO 2009/012468 |
| 382 | GAAGUUGUUCGUGGUGGAUUCG | 44 | WO 2009/012468 |
| 422a | ACUGGACUUAGGGUCAGAAGGC | 45 | US 12/391,028 |
| 378 | ACUGGACUUGGAGUCAGAAGG | 46 | WO 2009/012468 |
| 424 | CAGCAGCAAUUCAUGUUUUGAA | 47 | WO 2009/062169 |
| 483-3p | UCACUCCUCUCCUCCCGUCUU | 48 | WO 2009/012468 |
| 484 | UCAGGCUCAGUCCCCUCCCGAU | 49 | WO 2009/012468 |
| 486-5p | UCCUGUACUGAGCUGCCCCGAG | 50 | WO 2009/012468 |
| 497 | CAGCAGCACACUGUGGUUUGU | 51 | WO 2009/062169 |

TABLE 1-continued

| miRNA | miRNA Sequence | SEQ ID NO: | Reference |
|---|---|---|---|
| 499 | UUAAGACUUGCAGUGAUGUUU | 52 | WO 2009/018492 |
| 542-5p | UCGGGGAUCAUCAUGUCACGAGA | 53 | WO 2009/012468 |
| 92a | UAUUGCACUUGUCCCGGCCUGU | 54 | WO 2009/012468 |
| 92b | UAUUGCACUCGUCCCGGCCUCC | 55 | WO 2009/012468 |
| let-7a | UGAGGUAGUAGGUUGUAUAGUU | 56 | WO 2009/012468 |
| let-7b | UGAGGUAGUAGGUUGUGUGGUU | 57 | WO 2009/012468 |
| let-7c | UGAGGUAGUAGGUUGUAUGGUU | 58 | WO 2009/012468 |
| let-7d | AGAGGUAGUAGGUUGCAUAGUU | 59 | WO 2009/012468 |
| let-7e | UGAGGUAGGAGGUUGUAUAGUU | 60 | WO 2009/012468 |
| let-7f | UGAGGUAGUAGAUUGUAUAGUU | 61 | WO 2009/012468 |
| let-7g | UGAGGUAGUAGUUUGUACAGUU | 62 | WO 2009/012468 |
| 451 | AAACCGUUACCAUUACUGAGUU | 63 | US 61/286,546 |

The polynucleotide may carry from one to five lipophilic groups conjugated as described herein. The lipophilic groups may be conjugated through a polynucleotide 5' or 3' position, and/or conjugated to the polynucleotide backbone via formation of, for example, a phosphate ester. In certain embodiments, the polynucleotide carries one or two lipophilic groups at the 5' and/or 3' end, conjugated as described herein.

Pharmaceutical Compositions and Delivery

The conjugates of the invention may be formulated as a variety of pharmaceutical compositions. Pharmaceutical compositions will be prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Infralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are hereby incorporated by reference in their entireties.

The pharmaceutical compositions and formulations may employ appropriate salts and buffers to render delivery vehicles stable and allow for uptake by target cells. Aqueous compositions of the present invention comprise an effective amount of the delivery vehicle comprising the inhibitor polynucleotides or miRNA polynucleotide sequences (e.g. liposomes or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be by intradermal, subcutaneous, intramuscular, intraperitoneal or intravenous injection, or by direct injection into target tissue (e.g., cardiac tissue). Pharmaceutical compositions comprising miRNA inhibitors or expression constructs comprising miRNA sequences may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all hereby incorporated by reference in their entireties.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Methods of Treatment

The invention provides a method for delivering polynucleotides to a mammalian cell, and methods for treating, ameliorating, or preventing the progression of a condition in a mammalian patient. The method generally comprises administering the polynucleotide as a conjugate with cholesterol or other lipophilic moiety as described herein. The polynucleotide may be a miRNA or a miRNA inhibitor (e.g., having a nucleotide sequence designed to inhibit expression or activity of a miRNA). Thus, the patient may have a condition associated with RNA expression, such as miRNA expression. Such conditions include, for example, cardiac hypertrophy, myocardial infarction, heart failure (e.g., congestive heart failure), vascular damage, restenosis, or pathologic cardiac fibrosis.

miRNAs involved in conditions such as cardiac hypertrophy, myocardial infarction, heart failure (e.g., congestive heart failure), vascular damage, restenosis, and/or pathologic cardiac fibrosis, as well as sequences for targeting miRNA function are described in WO 2008/016924, WO 2009/062169, WO 2009/058818, WO 2009/018492, WO 2009/018493, WO 2009/012468, and WO 2007/070483, which are hereby incorporated by reference in their entireties. Such miRNAs and sequences are further listed in Table 1 and described herein.

The lipophilic polynucleotide conjugate may be delivered to the patient as a pharmaceutical composition or formulation as also described herein.

In certain embodiments, the patient has one or more risk factors including, for example, long standing uncontrolled hypertension, uncorrected valvular disease, chronic angina, recent myocardial infarction, congenital predisposition to heart disease and pathological hypertrophy. Alternatively or in addition, the patient may have been diagnosed as having a genetic predisposition to, for example, cardiac hypertrophy, or may have a familial history of, for example, cardiac hypertrophy.

In this aspect, the present invention may provide for an improved exercise tolerance, reduced hospitalization, better quality of life, decreased morbidity, and/or decreased mortality in a patient with heart failure or cardiac hypertrophy.

Methods of Synthesizing Conjugates

The invention further provides methods of synthesizing polynucleotides having lipophilic moieties conjugated at the 5' and/or 3' end, or conjugated to the polynucleotide backbone, through a hydrocarbon linker. In this aspect, the invention involves coupling the lipophilic moiety with a linear or cyclic hydrocarbon having terminal functional groups to prepare a first intermediate, and preparing a second intermediate having functional groups suitable for incorporation into a polynucleotide chain during solid phase polynucleotide synthesis. Alternatively, the method involves synthesizing cholesterol conjugates with polynucleotides, after synthesis of the polynucleotide is complete, using for example, carbonyl addition-elimination/reductive amination, amidation, maleimide-thiol coupling, aqueous Diels-Alder and "Click" chemistries.

In certain embodiments where the lipophilic moiety is an alcohol, such as a sterol, the method comprises conjugating the lipophilic moiety to a hydrocarbon (as described herein) that has terminal functional groups. This step will prepare a first intermediate, preferably an ether-linked intermediate. For example, in certain embodiments a sterol is etherized (through the sterol hydroxyl) to a C3-C15 hydrocarbon. The hydrocarbon in certain embodiments is a substantially linear C4-C8 (e.g., C4 or C6) hydrocarbon, which may be substituted, and which may have one, two, or three heteroatoms in the backbone independently selected from O, N and/or S. Alternatively, the hydrocarbon comprises a C5 to C8 cyclic hydrocarbon, e.g., cyclohexane, or a 5 to 8 membered cyclic group having one or two heteroatoms.

Figure 2:
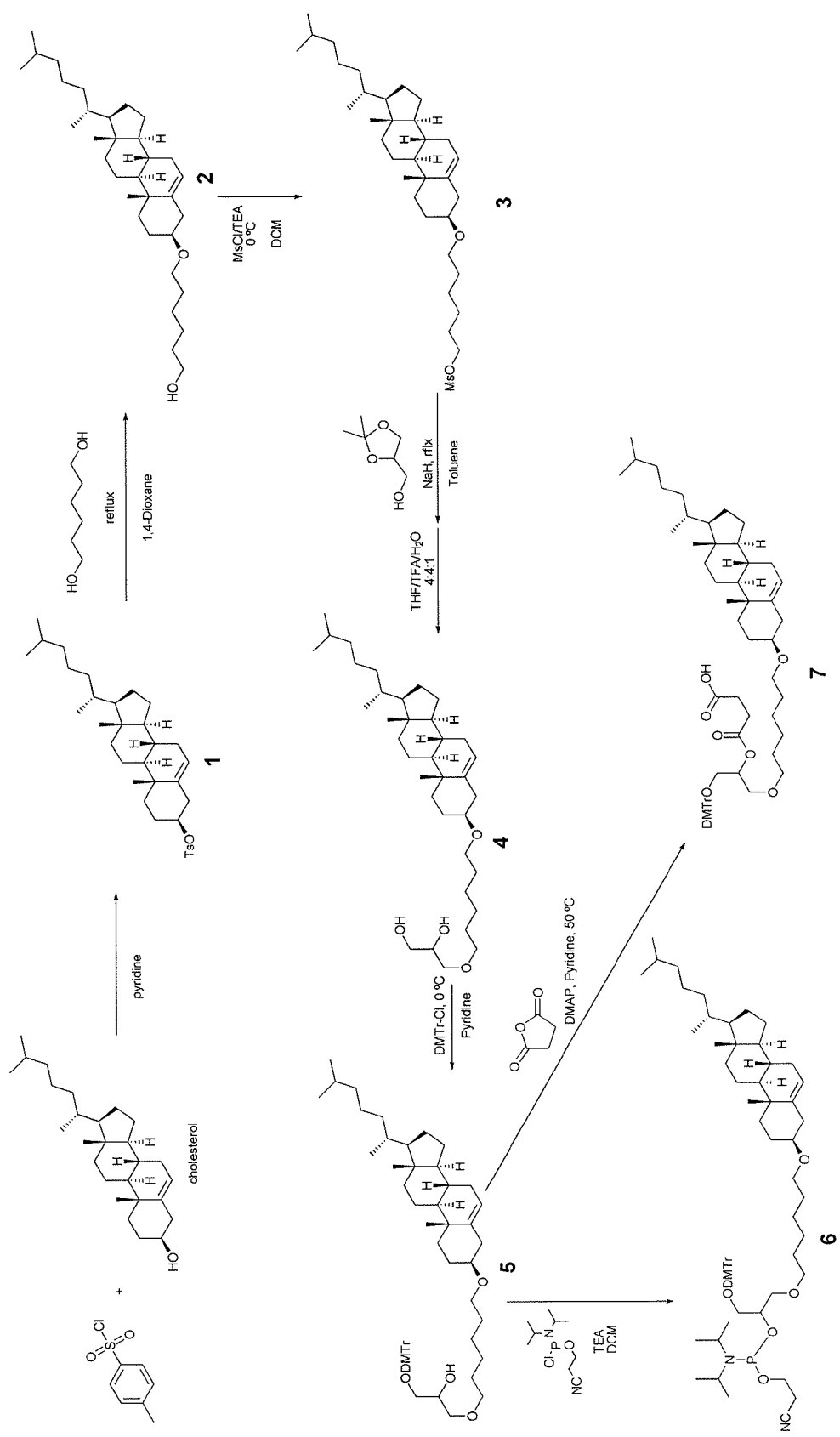
FIG. 2 illustrates the synthesis of exemplary conjugates in accordance with the invention, including the preparation of phosphoramidite intermediates for coupling to a nucleotide at the 5' position (6), and succinate intermediates for coupling to a solid support (7).

The first or ether-linked intermediate is further reacted to prepare a suitable second intermediate that is compatible with solid phase nucleic acid synthesis. For example, the ether-linked intermediate may be further reacted through one or more steps to prepare a phosphoramidite intermediate (e.g., through an ether linkage) for converting to a phosphate ester during polynucleotide synthesis. Alternatively, or in addition, the ether-linked intermediate may be further reacted through one or more steps to prepare a suitable terminal group for coupling (e.g. via amidation) to a suitable support to form the 3' end of a polynucleotide chain. Exemplary reactions for preparing 5' and 3' conjugates are illustrated in FIG. 2.

In certain embodiments involving the preparation of a phosphoramidite intermediate (shown as 6 in FIG. 2), the terminal alcohol of the ether-linked intermediate (2) is reacted to prepare the phosphoramidite by reaction with a phosphitylating agent, such as 2-cyanoethyl N,N-diisopropylchlorophosphoramidite. These embodiments may be employed particularly where there is no need for trityl monitoring or additional amidite couplings.

Alternatively, other intermediates having a suitable hydroxyl for phosphoramidite preparation may be synthesized from (2). For example, compound (2) may be reacted to form two differentiated hydroxyl groups separated by at least one carbon, but preferably 2 or more carbons. An exemplary series of reactions for converting compound (2) to a compound having differentiated hydroxyls (5) is shown in FIG. 2. Cholesterol tosylate (1), formed by reacting cholesterol with tosyl chloride, undergoes an Sn1 reaction with 1,6-hexanediol in refluxing 1,4-dioxane. Neighboring group participation by the alkene at the 5-position provides the 3β-isomer exclusively. The resultant (Cholest-5-en-3β-oxy)hexan-6-ol (2) is converted to the mesylate (3) which is subsequently used to alkylate solketal. The crude solketal derivative is deprotected by treatment with trifluoroacetic acid in wet THF to give 3-(6-(Cholest-5-en-3β-oxy)hexyloxy)propane-1,2-diol (4). The primary alcohol of the diol is selectively protected as the 4,4'-Dimethoxytrityl ether (5) using standard methods. The remaining secondary alcohol can be converted to the phosphoramidite (6) by reacting with a phosphitylating agent, such as 2-Cyanoethyl N,N-diisopropylchlorophosphoramidite, and subsequently used as a standard amidite monomer in the oligonucleotide synthesis cycle. Alternatively, the secondary alcohol can be converted to the succinate ester (7) by treatment with succinic anhydride in the presence of TEA. The resultant carboxylate can then be coupled, via HBTU, to excess amine functionalized controlled pore glass (CPG). The excess amines and any free surface hydroxides of the CPG are rendered unreactive by "capping" with acetic anhydride. The cholesterol functionalized CPG is suitable for 3'-cholesterol modified oligonucleotide synthesis. The CPG can be used just as any standard nucleoside loaded CPG is used in automated oligonucleotide synthesis.

Thus, in these embodiments the second intermediate is prepared from a compound having at least one 2°-alcohol and at least one 1°-alcohol. In accordance with these embodiments, during polynucleotide synthesis, one hydroxyl group forms a phosphodiester linkage with the nucleotide on the 5'-end of the chain. In the case of a 5' conjugate, two hydroxyl groups would allow for trityl monitoring of the reaction on an automated synthesizer and/or further chain elongation past the cholesterol conjugate, if desired.

In certain embodiments involving the preparation of a second intermediate for coupling to a solid support (shown as 7 in FIG. 2), the alcohol of the ether-linked intermediate (2) is reacted in several steps to prepare a succinate intermediate (or other intermediate cleavable from a solid support). Intermediates for preparing 3' conjugates would, as above, preferably have two hydroxyl groups, preferably differentiated. For example, the intermediate for coupling to a solid support may be prepared from a compound having at least one 2° hydroxyl and at least one 1° hydroxyl. An exemplary series of reactions for converting compound 2 to a compound having differentiated hydroxyls (5) is shown in FIG. 2. In these embodiments, during polynucleotide synthesis the nucleotide chain will grow off the DMTr-protected 1°-alcohol and the conjugate moiety will be anchored to a solid support via some type of cleavable linkage on the 2°-hydroxyl group (e.g., succinate).

Figure 4:
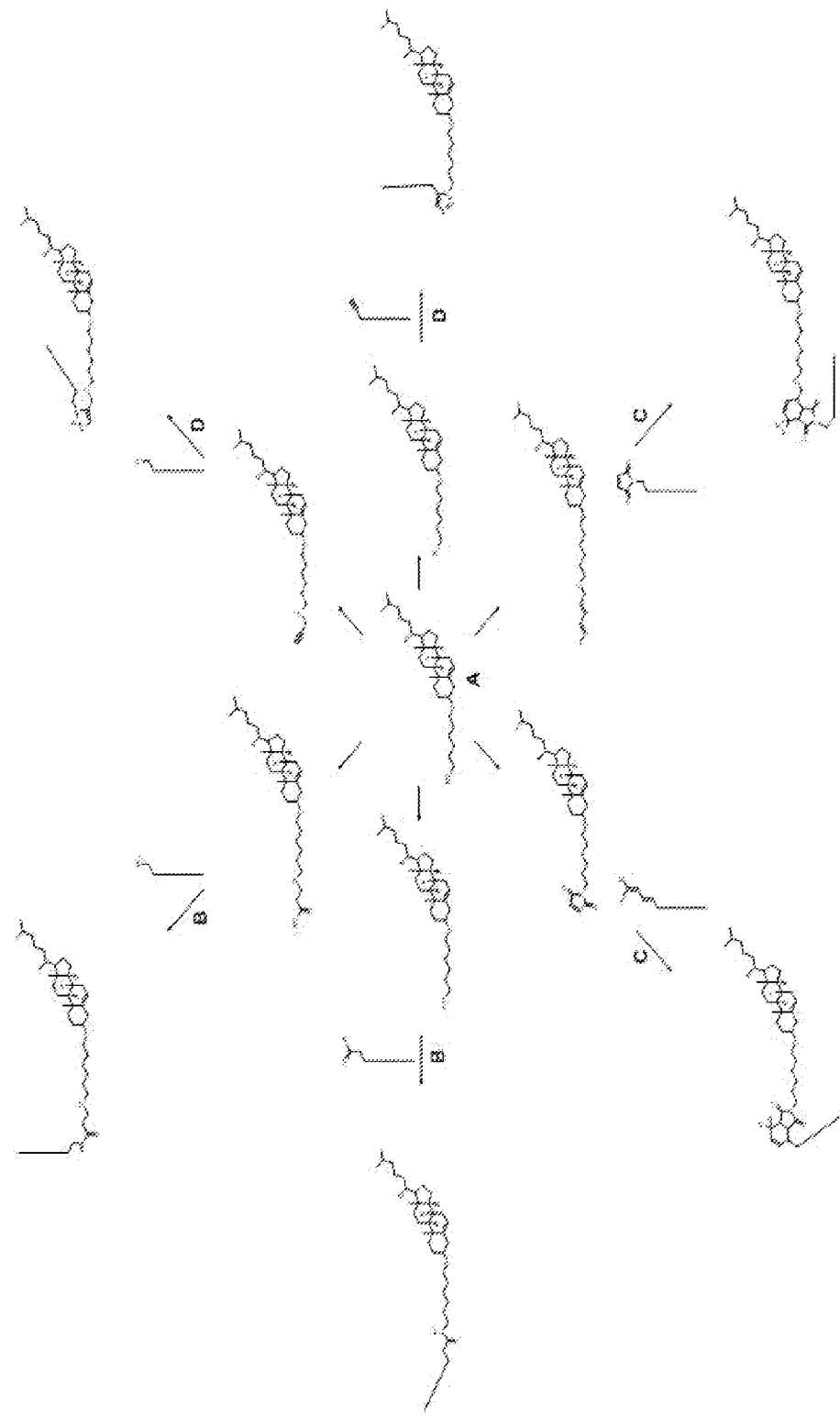
FIG. 4 illustrates that Cholest-5-en-3-oxyalkanol (A) can be modified to give functional groups amenable to common bioconjugation techniques such as amidation (B), Diels-Alder bioconjugation (C) and "Click" bioconjugation (D) when the oligonucleotide is functionalized with the complementary functional group.

Alternative embodiments of this invention includes the addition of a derivative of ether-linked intermediate (2) after oligonucleotide synthesis is complete. See FIG. 4. This can be accomplished, for example, via reactions as carbonyl addition-elimination/reductive amination, amidation, maleimide-thiol coupling, aqueous Diels-Alder and "Click" chemistries. These methods provide equivalent cholesterol ether constructs without the need to synthesize cholesterol-amidites. For example, a cholest-5-en-3β-oxyalkanol, such as compound (2), can be readily modified by one of skill in the art to give a terminal aldehyde, carboxylate, amine, maleimide, thiol, diene, azide, alkyne or other reactive moiety. These compounds can be further reacted with an oligonucleotide suitably modified with a complimentary functional group that forms a covalent bond with the reactive moiety of the terminally fuctionalized cholest-5-en-3β-oxyalkane. The product is a cholesterol conjugate that still retains a relatively nonpolar, substantially linear alkyloxy linkage to the cholesterol moiety, and maintains a 3 or greater atom distance between the lipophillic moiety and any group containing an exchangeable proton or other substantially polar functional group. These so-called "post-synthetic bioconjugations" can be performed while the protected synthetic oligonucleotide chain is still attached to the solid phase, or after deprotection when the synthetic oligonucleotide is in solution.

Techniques for bioconjugation are well known, and are described, for example, in Hermanson GT, Bioconjugate Techniques, Second Edition, Academic Press; 2nd edition (Apr. 1, 2008).

EXAMPLES

Nucleic acid (NA)-Chol conjugates have been derived from amines reacted with readily available cholesterol chloroformate to give a carbamate linkage at the 3β position of the cholestene ring structure. This system places a polar group with an exchangeable hydrogen very close to the lipophilic ring structure. This can limit the lipophilicity of the conjugate and the ability of conjugate to fully intercalate into any lipid bilayer or associate with other lipophilic moieties. See FIG. 1. The conjugates as described herein avoid the use of linker groups that place polar groups with exchangeable protons next to the cholestene ring structure (FIG. 1).

Example 1

Synthesis of Exemplary Conjugates

An ether linked cholesterol, such as Chol-O-HEX-OH (shown as 2 in FIG. 2) may be used to create NA conjugates. FIG. 2 depicts the synthesis of a linker amidite, 6, and succinate, 7 (herein referred to as "C6-Chol"). They may be used, respectively, as a 5'-modification (Compound 6) on a common, chemically synthesized oligonucleotide made with normally available synthesis reagents and as a 3'-modification (Compound 7) when conjugated via amidation to any commercially available amino support used for oligonucleotide synthesis. An amidite may alternatively be prepared from an alcohol such as 2 for 5'-terminally conjugated oligonucleotides, for example, when there is no need for trityl monitoring or additional amidite couplings.

Generally, the hydrocarbon spacer contains a hydroxyl group at or near the terminus to form a phosphate ester. Preferably, there are two hydroxyl groups that would be separated by at least one carbon, but preferably 2 or more carbons. For example, the hydroxyls may be differentiated where one is a 2°-alcohol and the other is a 1°-alcohol. At least one hydroxyl group is necessary to form a phosphodiester linkage with the nucleotide on the 5'-end of the chain. In the case of a 5'-cholesterol conjugate, two hydroxyl groups would allow for trityl monitoring of the reaction on an automated synthesizer and/or further chain elongation past the cholesterol conjugate. The 4,4'-dimethoxytrityl (DMTr) would be placed, for example, on one hydroxyl and the phophoramidite (i.e. the phosphodiester precursor) would be on the remaining hydroxyl, which provides for more efficient phosphoramidite coupling.

3'-Cholesterol conjugates would require two hydroxyl groups, preferably differentiated (i.e. one is 2° and one is) 1° where the nucleotide chain would grow off the DMTr-protected 1°-alcohol and the where the conjugate moiety would be anchored to a solid support via some type of cleavable linkage on the 2°-hydroxyl group. The 5'-conjugate would have the phosphate on the 2° position.

An exemplary synthesis of Chol-O-Hex intermediates for conjugation during solid phase polynucleotide synthesis are described below.

Cholest-5-en-3β-tosylate

Cholesterol (25.0 g, 64.7 mmol) is weighed into a 500 mL round bottomed flask and dissolved in pyridine (200 mL) to give a colorless solution that is cooled to 0° C. Tosyl chloride (24.65 g, 129 mmol) is weighed into a 100 mL round bottomed flask and dissolved in pyridine (40 mL) to give a slightly yellow solution. The tosyl chloride solution is then added, at once, to the stirring cholesterol solution and the resultant reaction mixture is allowed to stir overnight while coming to room temperature. The reaction mixture is concentrated on a rotary evaporator to give a white solid that is taken up in minimum amount of chloroform (40 mL) and precipitated via addition of methanol (500 mL). The resultant white solid is filtered and washed with methanol (500 mL) and acetonitrile (200 mL). The solid is transferred to a 1 L round bottomed flask and dried overnight under high vacuum to give 34.2 g (98%) of a white powder. $^1$H (400 MHz, CDCl3): δ0.67 (3H, s); 0.80-1.75 (33H, m); 1.76-2.03 (5H, m); 2.20-2.30 (1H, m); 2.44 (4H, m); 4.25-4.35 (1H, m); 5.29 (1H, d, J=5 Hz); 7.32 (2H, d, J=8 Hz); 7.79 (2H, d, J=8 Hz).

Cholest-5-en-3β-oxyhexan-6-ol

Cholest-5-en-3β-tosylate (15.0 g, 27.7 mmol) and 1,6-hexanediol (65.5 g, 555 mmol) is weighed into a 500 mL round bottomed flask and dissolved in 1,4-dioxane (300 mL) to give a colorless suspension. The flask is fitted with an efficient reflux condenser and the reaction mixture is heated to reflux in a 110° C. oil bath for 17 hr. The reaction mixture is concentrated in vacuo and the residue is suspended in DI water (500 mL). The aqueous phase is extracted with EtOAc (2×150 mL) and the combined organic phases are washed with water (2×300 mL) and brine (1×150 mL). The organic phase is dried over sodium sulfate, filtered, concentrated and dried overnight under high vacuum to give 12.85 g (95%) of a light yellow wax. $^1$H (400 MHz, CDCl$_3$): δ0.67 (3H, s); 0.80-1.65 (42H, m); 1.75-2.05 (5H, m); 2.12-2.25 (1H, m); 2.30-2.40 (1H, m); 3.05-3.17 (1H, m); 3.45 (2H, dt, J=6.5, 1.6 Hz); 3.57 (2H, t, J=6.6 Hz); 5.34 (1H, d, J=5.3 Hz).

Cholest-5-en-3β-oxyhexan-6-mesylate

Cholest-5-en-3β-oxyhexan-6-ol (12.84 g, 26.4 mmol) is weighed into a a 500 mL round bottomed flask. The flask is charged with dichloromethane (100 mL) and triethylamine (7.35 mL, 52.7 mmol), flushed with argon and cooled to 0° C. Mesyl chloride (2.55 mL, 32.96 mmol) is added dropwise over 5 minutes to the stirring solution and the mixture is allowed to stir for an additional 1 h at 0° C. Saturated sodium bicarbonate solution (150 mL) was added to the mixture which was then transferred to a separatory funnel. The aqueous phase was discarded and the organic phase washed with fresh saturated sodium bicarbonate solution (1×150 mL) and brine (1×50 mL). The organic phase is dried over Na$_2$SO$_4$, filtered and concentrated to dryness to give 14.8 g (99%) of a yellow wax. $^1$H (400 MHz, CDCl$_3$): δ0.67 (3H, s); 0.80-1.65 (41H, m); 1.70-2.05 (5H, m); 2.12-2.23 (1H, m); 2.30-2.37 (1H, m); 3.00 (3H, s); 3.05-3.17 (1H, m); 3.45 (2H, dt, J=6.5, 1.4 Hz); 4.22 (2H, t, J=6.6 Hz); 5.34 (1H, d, J=5.2 Hz).

3-(6-(Cholest-5-en-3β-oxy)hexyloxy)propane-1,2-diol

Solketal (2.92 g, 27.5 mmol) was weighed into a 200 mL round bottomed flask. The flask was flushed with argon and charged with toluene (40 mL). Sodium hydride, 60% dispersion in oil (3.14 g, 131 mmol) was added, at once, to the stirring solution and the mixture was allowed to stir for 30 minutes at room temperature. Cholest-5-en-3β-oxyhexan-6-mesylate (14.8 g, 26.2 mmol) was dissolved in toluene (40 mL) and the solution was added slowly to the alkoxide solution. The flask was fitted with a reflux condenser and the apparatus flushed with argon. The reaction mixture was heated to reflux and allowed to stir for 17 hrs. The reaction mixture was cooled to room temperature and quenched with a solution of ethanol in ethyl acetate added dropwise to the vigorously stirred reaction mixture over 15 minutes. The reaction mixture was further diluted with ethyl acetate and washed with 10% aqueous sodium carbonate solution (2×150 mL). The organic phase was dried over Na$_2$SO$_4$, filtered and concentrated.

The residue was re-dissolved in a 4:4:1 ratio of tetrahydrofuran:trifluoroacetic:water (18 mL), then set to stir for 2 hours at room temperature. TLC (15% acetone/hexanes) of the reaction mixture revealed that the deprotection of the desired compound in the crude mixture was complete. The reaction mixture was evaporated to dryness, applied to a 100 g Biotage SNAP silica column and eluted with an ethyl acetate/hexanes gradient (0-35% over 2 L @~50 mL/min) to give 4.90 g (33% over two steps) of a colorless wax. $^1$H (400 MHz, CDCl$_3$): δ0.67 (3H, s); 0.80-1.65 (41H, m); 1.75-2.05 (5H, m); 2.12-2.40 (4H, m); 3.07-3.17 (1H, m); 3.40-3.57 (6H, m); 3.63 (1H, dd, J=11.4, 5.2); 3.71 (1H, dd, J=11.4, 3.9); 3.81-3.89 (1H, m); 5.34 (1H, d, J=5.2 Hz).

1-(4,4'-Dimethoxytrityloxy)-3-(6-(Cholest-5-en-3β-oxy)hexyloxy)propan-2-ol 3-(6-(Cholest-5-en-3β-oxy)hexyloxy)propane-1,2-diol (4.75 g, 8.47 mmol) was weighed into a 200 mL round bottomed flask with a stir bar. The flask was flushed with argon, charged with pyridine (30 mL) and cooled to 0° C. with stirring. DMTr-CI (3.01 g, 8.89 mmol) was weighed into a 20 mL scintillation vial and dissolved in pyridine (17 mL). The DMTr-CI solution was added, dropwise, to the stirring diol solution over 20 minutes. The reaction was allowed to stir overnight while coming to room temperature. The reaction was quenched by adding anhydrous methanol (1 mL) and allowing the reaction to stir for 30 minutes. Saturated sodium bicarbonate solution (50 mL) was added to the reaction mixture, which was stirred until CO$_2$ evolution ceased. The mixture was concentrated to dryness and partitioned with water (100 mL) and ethyl acetate (100 mL). The organic phase was dried over Na2SO4, filtered and concentrated. The residue was applied to a 100 g Biotage SNAP column and eluted with an ethyl acetate/hexanes gradient (10-20% over 1.5 L @~50 mL/min) to give 3.50 g (47.9%) of a colorless, sticky oil. $^1$H (400 MHz, CDCl$_3$): δ0.67 (3H, s); 0.87 (6H, dd, J=6.6, 1.8 Hz); 0.91 (3H, d, J=6.6 Hz); 0.93-1.60 (32H, m); 1.75-2.05 (5H, m); 2.15-2.25 (1H, m); 2.32-2.41 (1H, m); 2.42 (1H, d, J=4.6 Hz); 3.07-3.22 (2H, m); 3.39-3.57 (6H, m); 3.79 (6H, s); 3.80 (s, 1H); 3.90-3.98 (1H, m); 5.34 (1H, d, J=5.3 Hz); 6.78-6.85 (m, 4H); 7.14-7.25 (m, 1H); 7.26-7.34 (m, 6H); 7.40-7.44 (m, 2H).

4-(4,4'-Dimethoxytrityloxy)-3-(6-(Cholest-5-en-3β-oxy)hexyloxy)propan-2-yloxy)-4-oxobutanoic Acid, TEA Salt 1-(4,4'-Dimethoxytrityloxy)-3-(6-(Cholest-5-en-3β-oxy)hexyloxy)propan-2-ol (1.75 g, 2.02 mmol), succinic anhydride (0.812 g, 8.10 mmol) and 4-(dimethylamino)pyridine (25 mg, 0.20 mmol) was added to a 100 mL round bottomed flask with a stir bar. The flask was charged with pyridine (10 mL). The reaction mixture was stirred for 8 hours at 80° C. and 16 h at 50° C. The reaction mixture was concentrated in vacuo and co-evaporated with EtOH (3×20 mL) to remove residual pyridine. The residue was applied to a 50 g Biotage SNAP column and eluted @~40 mL/min with 1 L of 60/30/10 EtOAc/Hex/MeOH with 3% TEA followed by 500 mL of 90/10 DCM/MeOH with 3% TEA to give 1.31 g (61%) of a colorless wax. $^1$H (400 MHz, CDCl$_3$): δ0.67 (3H, s); 0.86 (6H, dd, J=6.6, 1.8 Hz); 0.91 (3H, d, J=6.6 Hz); 0.93-1.60 (41H, m); 1.75-2.05 (5H, m); 2.15-2.25 (1H, m); 2.32-2.41 (1H, m); 2.51-2.72 (4H, m); 2.97 (6H, q, J=7.3 Hz); 3.07-3.25 (2H, m); 3.31-3.48 (4H, m); 3.52-3.61 (2H, m); 3.78 (6H, s); 5.19 (1H, quintet, J=5.1 Hz); 5.35 (1H, d, J=5.4 Hz); 6.78-6.85 (m, 4H); 7.14-7.25 (m, 1H); 7.26-7.34 (m, 6H); 7.40-7.44 (m, 2H).

"Chol-O-Hex-LCAA-CPG"

4-(4,4'-Dimethoxytrityloxy)-3-(6-(Cholest-5-en-3β-oxy)hexyloxy)propan-2-yloxy)-4-oxobutanoic acid, TEA salt (1.00 g, 0.952 mmol) is weighed into a 20 mL scintillation vial. The vial is charged with 6 mL of 2:1 ACN:DCM. HBTU (0.343 g, 0.904 mmol) is added to the succinate followed by triethylamine (0.25 mL). In a 200 mL round bottomed flask is weighed LCAA-CPG (12.56 g) with a loading of 132 µmol/g amine. The CPG is suspended in 75 mL of 2:1 ACN:DCM. The succinate/HBTU mixture is added, at once, to the LCAA-CPG suspension, the flask is sealed and the combined mixture is agitated on an incubated orbital shaker at 25° C. @250 rpm for 4 hours. The CPG is filtered and washed with 200 mL aliquots of ACN, DCM, DMF, water, methanol, ACN and DCM. The CPG is air dried overnight. The CPG is then transferred to a clean 200 mL round bottomed flask. The flask is charged with 40 mL of CAP A solution and 40 mL of CAP B solution, septum sealed and the contents agitated at 25° C. @250 rpm for 3 hours. The CPG is then filtered and washed thoroughly with 200 mL aliquots of ACN, DCM, MeOH, H2O, MeOH, DMF, ACN, DCM. The CPG is air dried overnight.

The CPG loading is measured by a modification of the method described by Pon, R. T., *Current Protocols in Nucleic Acid Chemistry*. 2000 3.2.1-3.2.23. CPG (4.24 mg) was weighed into a 20 mL scintillation vial. 5% Trifluoroacetic acid in dichloroethane was added and the vial was capped and shaken for 1 minute. The absorbance of the solution was measured at 503 nm via a ThermoSpectronic Genesys10 UV/Vis spectrophotometer to be 2.114. The loading was calculated by the formula:

[(volume, mL×absorbance)/76 mLcm$^{-1}$µmol$^{-1}$]×
[1000/mass, mg]=loading in µmol/g to give: [(10 mL×2.114)/76 mLcm$^{-1}$µmol$^{-1}$]×[1000/4.24 mg]=66 µmol/g.

"Chol-O-Hex-DMTr Amidite"

1-(4,4'-Dimethoxytrityloxy)-3-(6-(Cholest-5-en-3β-oxy)hexyloxy)propan-2-ol (1.68 g, 1.95 mmol) is weighed into a 200 mL round bottomed flask with a stir bar. The flask is flushed with argon, septum sealed and charged with DCM (10 mL) and N,N-diisopropylethylamine (0.68 mL, 3.89 mmol). 2-Cyanoethyl N,N-diisopropylchlorophosphoramidite (0.48 g, 2.0 mmol) is added to the stirring reaction dropwise and the reaction is allowed to stir for 17 hrs. The reaction mixture is diluted with DCM 50 mL and washed with saturated bicarbonate solution (2×50 mL) and brine (1×50 mL). The organic phase is dried over Na$_2$SO$_4$, filtered and concentrated. The residue is applied to a 25 g Biotage SNAP column and eluted with an ethyl acetate/hexanes gradient (5-10% over 750 mL @25 mL/min) to give 1.70 g (82.1%) of a white foam. $^1$H (400 MHz, DMSO-d6): δ0.62 (3H, s); 0.80-1.57 (53H, m); 1.70-1.95 (5H, m); 1.96-2.02 (1H, m); 2.21-2.26 (1H, m); 2.57-2.72 (2H, d, J=4.6 Hz); 2.97-3.80 (m, 20H); 3.97 (1H, quintuplet, J=5.3 Hz); 5.26 (1H, d, J=4.6 Hz); 6.78-6.86 (m, 4H); 7.13-7.29 (m, 7H); 7.34-7.39 (m, 2H).

Example 2

Figure 3:
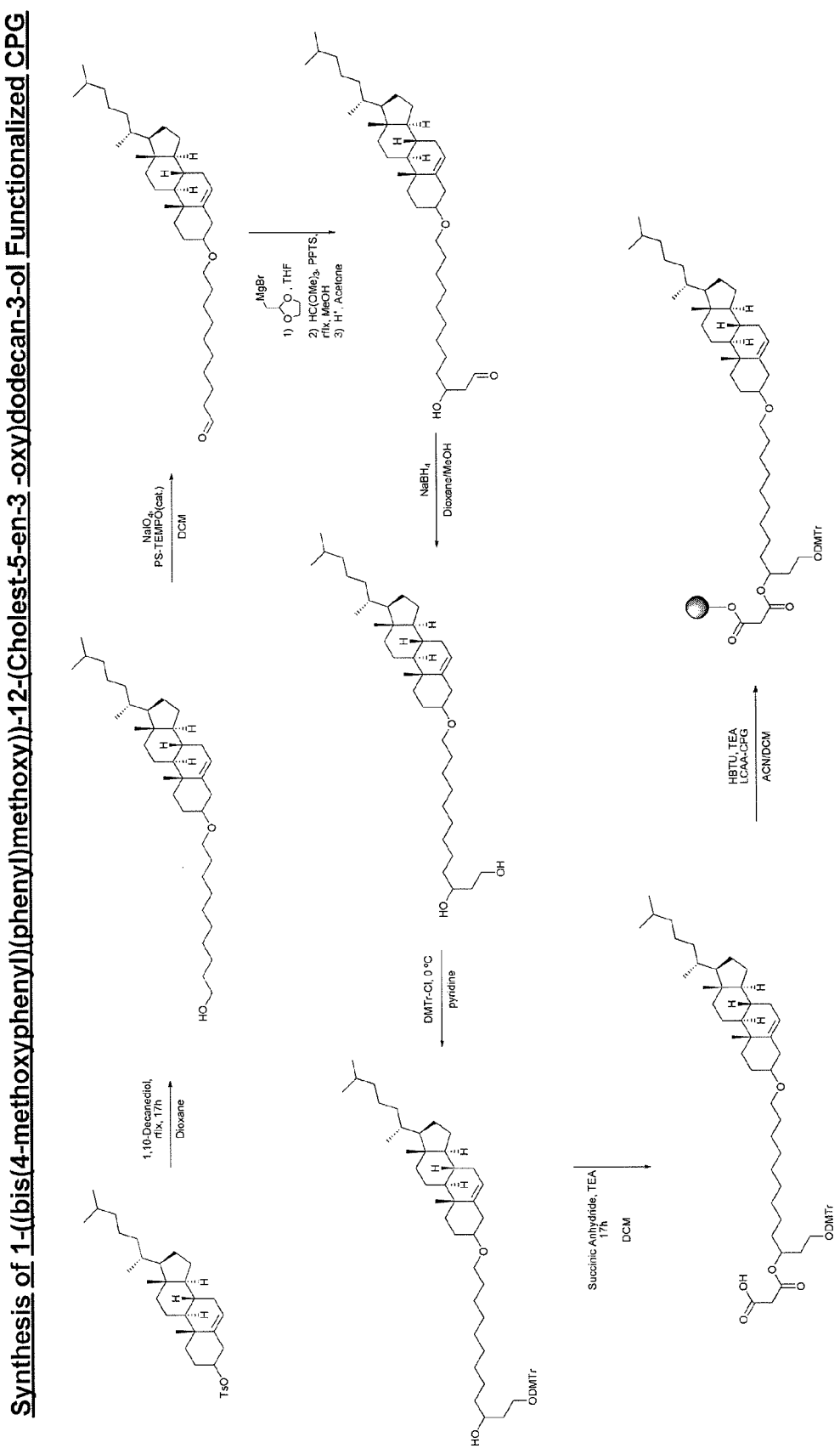
FIG. 3 illustrates the synthesis of an exemplary 3'-cholesterol conjugate (1-((bis(4-methoxyphenyl)(phenyl)methoxy))-12-(Cholest-5-en-3β-oxy)dodecan-3-ol Functionalized CPG) with the cholesterol-linked intermediate anchored to a solid support.

Synthesis of 1-((bis(4-methoxyphenyl)(phenyl)methoxy))-12-(Cholest-5-en-3-oxy)dodecan-3-ol Functionalized CPG FIG. 3 depicts the synthesis of a linker structure (III) described herein that can be used as a polynucleotide 3'-modification. The synthesis steps are described in more detail below.

10-(Cholest-5-en-3β-oxy)decan-1-ol

In a 500 mL round-bottomed flask was cholesteryl tosylate (10.0 g, 18.5 mmol) and 1,10-Decanediol (48.3 g, 277 mmol) suspended in Dioxane (200 ml) to give a white suspension. The flask was fitted with a temperature sensor and reflux condenser. The mixture was heated to reflux and allowed to stir at reflux overnight. The reaction mixture was cooled to room temperature and the solids were filtered off. The solution was concentrated in vacuo. The mixture was re-dissolved in methanol (250 mL) and water (ca. 40 mL) was added to precipitate out the crude product. The precipitate was filtered and dried in vacuo. The residue was further purified via column chromatography on a 100 g Biotage SNAP column eluting over 2 L of a 0-25% EtOAc in Hexanes gradient. Pure fractions were combined and concentrated to give 7.85 g (82%) of a white solid. $^1$H NMR (300 mHz, CDCl$_3$) δ0.69 (3H, s); 0.85-1.66 (50H, m); 1.75-2.09 (5H, m); 2.14-2.29 (1H, m); 2.32-2.43 (1H, m); 3.14 (1H, tt, J=11.2, 4.4 Hz); 3.46 (2H, dt, J=6.9, 0.4 Hz); 3.65 (2H, t, J=6.6 Hz); 5.36 (1H, d, J=5.3 Hz).

10-(Cholest-5-en-3β-oxy)decanal

In a 100 mL round-bottomed flask was solid supported 2,2,6,6-Tetramethyl Piperidinyloxy, Free Radical (0.5 g, 1.1 mmol/g, 0.553 mmol) and 10-(Cholest-5-en-3β-oxy)decan-1-ol (3.00 g, 5.53 mmol) suspended in dichloromethane (20 ml) to give a colorless suspension. Iodobenzene diacetate (1.958 g, 6.08 mmol) was added to the mixture, which was allowed to stir overnight at room temperature. The reaction mixture was filtered and the solid support washed with DCM. The combined filtrate was washed with saturated sodium thiosulfate (2×20 mL) and brine (1×20 mL). The organic phase was dried over Na$_2$SO$_4$, filtered and concentrated. The resultant oil was purified via column chromatography with 100% DCM as mobile phase to give 2.70 g (90%) of a colorless wax. $^1$H NMR (300 MHz, CDCl$_3$) δ0.69 (3H, s); 0.84-1.74 (47H, m); 1.76-2.09 (5H, m); 2.12-2.26 (1H, m); 2.32-2.40 (1H, m); 2.44 (2H, dt, J=7.4, 1.9 Hz); 3.14 (1H, tt, J=11.2, 4.4 Hz); 3.46 (2H, t, J=6.9 Hz); 5.35 (1H, d, J=5.3 Hz); 9.78 (1H, t, J=1.9 Hz).

12-(Cholest-5-en-3β-oxy)-3-hydroxydodecanal

In a dry 200 mL round-bottomed flask was 10-(Cholest-5-en-3β-oxy)decanal (2.65 g, 4.90 mmol) dissolved in THF (10 ml), under argon to give a colorless solution. A 0.5 M THF solution of ((1,3-dioxolan-2-yl)methyl)magnesium bromide (9.80 ml, 4.90 mmol) was added dropwise, and the resulting solution was allowed to stir for 4 h at room temperature. The resultant solution was quenched by slowly adding 100 mL of NaHCO$_3$ solution and extracting with EtOAc (3×100 mL). The combined organic phase was washed with brine (1×100 mL), dried over sodium sulfate, filtered and concentrated in a 500 mL round bottomed flask. Trimethyl orthoformate (10.83 ml, 98 mmol), PPTS (0.246 g, 0.980 mmol) and methanol (10 ml) were added to the flask and the contents brought to reflux for 2 h. The solution was cooled to room temperature and evaporated to dryness. The residue was then taken up in Acetone (20 ml) and 1.0N HYDROCHLORIC ACID (4.90 ml, 4.90 mmol) and allowed to stir overnight. The reaction mixture was diluted to 200 mL with water and extracted with ethyl acetate (3×100 mL). The organic phase was combined, washed with brine (1×50 mL), dried over $Na_2SO_4$, filtered and concentrated. The resultant wax was purified via column chromatography on a 40 g Biotage SNAP column eluting with a 0-50% gradient over 1 L. The pure fractions were combined and evaporated to dryness to give 12-(Cholest-5-en-3β-oxy)-3-hydroxydodecanal (1.97 g, 3.37 mmol, 68.7% yield) as a colorless wax. $^1$H NMR (300 MHz, $CDCl_3$) δ0.69 (3H, s); 0.85-1.74 (49H, m); 1.75-2.13 (7H, m); 2.14-2.28 (1H, m); 2.33-2.44 (1H, m); 3.14 (1H, tt, J=11.2, 4.4 Hz); 3.46 (2H, t, J=6.8 Hz); 3.93-4.10 (1H, m); 5.36 (1H, d, J=5.2 Hz); 5.42-5.55 (1H, m); 9.78 (1H, s).

12-(Cholest-5-en-3β-oxy)dodecan-1,3-diol

In a 100 mL round-bottomed flask was 12-(Cholest-5-en-3β-oxy)-3-hydroxydodecanal (1.90 g, 3.25 mmol) dissolved in 1,4-Dioxane (10 ml) to give a colorless solution. MeOH (5 ml) was added slowly and only enough was added to keep the aldehyde in solution. SODIUM BOROHYDRIDE (0.184 g, 4.87 mmol) was added to the stirring solution which was then allowed to stir for 2 hours at room temperature. The reaction mixture was quenched by addition of 1N HCl (2 mL). The mixture was diluted to 100 mL with water and extracted with ethyl acetate (3×50 mL). The organic phase was combined, washed with brine (1×50 mL), dried over $Na_2SO_4$, filtered and concentrated to give 12-(Cholest-5-en-3β-oxy)dodecan-1,3-diol (1.85 g, 3.15 mmol, 97% yield) as a colorless wax. $^1$H NMR (300 MHz, $CDCl_3$) δ0.69 (3H, s); 0.83-2.07 (58H, m); 2.13-2.28 (1H, m); 2.32-2.43 (1H, m); 3.14 (1H, tt, J=11.2, 4.4 Hz); 3.46 (2H, t, J=6.8 Hz); 3.60-4.19 (3H, m); 5.36 (1H, d, J=5.2 Hz).

1-((bis(4-methoxyphenyl)(phenyl)methoxy))-12-(Cholest-5-en-3β-oxy)dodecan-3-ol

In a 100 mL round-bottomed flask was 12-(Cholest-5-en-3(3-oxy)dodecan-1,3-diol (1.80 g, 3.07 mmol) dissolved in Pyridine (20 ml) to give a colorless solution. The mixture was cooled to 0° C., under argon with stirring. DMTr-CI (1.091 g, 3.22 mmol) was weighed into a septum sealed scintillation vial and dissolved in Pyridine (10 ml) to give a yellow solution. The DMTr-CI solution was added dropwise to the diol. The reaction mixture was stirred overnight while coming to room temperature. Methanol (2 mL) was added and the mixture allowed to stir an additional 15 minutes. The reaction mixture was diluted to 200 mL with saturated $NaHCO_3$ solution and extracted with ethyl acetate (3×50 mL). The organic phase was combined, washed with brine (1×50 mL), dried over $Na_2SO_4$, filtered and concentrated. The resultant oil was purified via a 40 g Biotage SNAP column eluted with a 0-50% EtOAc in Hexanes gradient over 1 L. The pure fractions were combined and evaporated to give 1-((bis(4-methoxyphenyl) (phenyl)methoxy))-12-(Cholest-5-en-3(3-oxy)dodecan-3-ol (2.60 g, 2.92 mmol, 95% yield) as a colorless oil. $^1$H NMR (300 MHz, $CDCl_3$) δ0.69 (3H, s); 0.83-2.09 (57H, m); 2.14-2.29 (1H, m); 2.33-2.44 (1H, m); 3.07-3.22 (3H, m); 3.47 (2H, t, J=6.9 Hz); 3.53-3.66 (1H, m); 3.81 (6H, s); 5.37 (1H, d, J=5.2 Hz); 6.80-6.88 (4H, m), 7.20-7.35 (7H, m); 7.40-7.49 (2H, m).

4-((1-(bis(4-methoxyphenyl)(phenyl)methoxy)-12-(Cholest-5-en-3β-oxy)dodecan-3-yl)oxy)-4-oxobutanoic Acid In a 20 mL scintillation vial was 1-((bis(4-methoxyphenyl) (phenyl)methoxy))-12-(Cholest-5-en-3β-oxy)dodecan-3-ol (0.5 g, 0.562 mmol) and succinic anhydride (0.113 g, 1.124 mmol) in DCM (10 ml) to give a colorless solution. TEA (0.313 ml, 2.249 mmol) was added and the mixture set to stir for 17 hours. The reaction was judged complete by TLC (25% EtOAc/Hex, PMA visualization). The reaction mixture was washed with 5% $NaHPO_4$ solution (3×15 mL) and brine (1×15 mL). The organic phase was dried over sodium sulfate, filtered and concentrated to dryness for use without further purification. $^1$H NMR (300 MHz, $CDCl_3$) δ0.70 (3H, s); 0.83-1.74 (49H, m); 1.77-2.12 (5H, m); 2.14-2.29 (1H, m); 2.33-2.44 (1H, m); 2.53-2.72 (4H, m); 3.00-3.09 (2H, m); 3.16 (1H, tt, J=11.2, 4.4 Hz); 3.48 (2H, t, J=6.8 Hz); 3.80 (6H, s); 4.85-5.00 (1H, m); 5.36 (1H, d, J=5.1 Hz); 6.78-6.90 (4H, m), 7.15-7.38 (7H, m); 7.40-7.49 (2H, m); 9.29 (1H, bs).

1-((bis(4-methoxyphenyl)(phenyl)methoxy))-12-(Cholest-5-en-3β-oxy)dodecan-3-ol Functionalized CPG 4-((1-(bis(4-methoxyphenyl)(phenyl)methoxy)-12-(Cholest-5-en-3β-oxy)dodecan-3-yl)oxy)-4-oxobutanoic acid (0.35 g, 0.36 mmol) is weighed into a 20 mL scintillation vial. The vial is charged with 6 mL of 2:1 ACN:DCM. HBTU (0.137 g, 0.35 mmol) is added to the succinate followed by triethylamine (0.25 mL). In a 100 mL round bottomed flask is weighed LCAA-CPG (5.00 g) with a loading of 132 μmol/g amine. The CPG is suspended in 30 mL of 2:1 ACN:DCM. The succinate/HBTU mixture is added, at once, to the LCAA-CPG suspension, the flask is sealed and the combined mixture is agitated on an incubated orbital shaker at 25° C. @250 rpm for 4 hours. The CPG is filtered and washed with 200 mL aliquots of ACN, DCM, DMF, water, methanol, ACN and DCM. The CPG is air dried overnight. The CPG is then transferred to a clean 200 mL round bottomed flask. The flask is charged with 40 mL of CAP A solution and 40 mL of CAP B solution, septum sealed and the contents agitated at 25° C. @250 rpm for 3 hours. The CPG is then filtered and washed thoroughly with 200 mL aliquots of ACN, DCM, MeOH, H2O, MeOH, DMF, ACN, DCM. The CPG is air dried overnight.

The CPG loading is measured by a modification of the method described by Pon, R. T., *Current Protocols in Nucleic Acid Chemistry.* 2000 3.2.1-3.2.23. CPG (4.24 mg) was weighed into a 20 mL scintillation vial. 5% Trifluoroacetic acid in dichloroethane was added and the vial was capped and shaken for 1 minute. The absorbance of the solution was measured at 503 nm via a ThermoSpectronic Genesys10 UV/Vis spectrophotometer to be 2.114. The loading was calculated by the formula:

[(volume, mL×absorbance)/76 mLcm$^{-1}$μmol$^{-1}$]× [1000/mass, mg]=loading in μmol/g to give:

[(10 mL×2.260)/76 mLcm$^{-1}$μmol$^{-1}$]×[1000/5.12 mg]=58 μmol/g

Example 3

Post-synthetic Addition of Cholesterol

The post synthetic addition of cholesterol via such reactions as carbonyl addition-elimination/reductive amination, amidation, maleimide-thiol coupling, aqueous Diels-Alder and "Click" would also provide equivalent cholesterol ether constructs without the need to synthesize cholesterol-amidites. For example, cholesterol tosylate may be alkylated to give a Cholest-5-en-3β-oxyalkanol that can be further modified to give a terminal aldehyde, carboxylate, amine, maleimide, thiol, diene, azide, alkyne or other reactive moiety that could be further reacted with a suitably modified oligonucleotide to give a cholesterol conjugate that still retains a substantially non-polar, substantially linear alkyloxy linkage to the cholesterol moiety, and that maintains a 3 or greater atom distance between the lipophillic moiety and any group containing an exchangeable proton or other substantially polar functional group. See FIG. 4.

Cholest-5-en-3-oxyalkanol (A) can be modified to give functional groups amenable to common bioconjugation techniques such as amidation (B), Diels-Alder bioconjugation (C) and "Click" bioconjugation (D) when the oligonucleotide is functionalized with the complementary functional group.

Example 4

In vivo Cardiac Knockdown of miR-208

For all chemistries indicated in Table 2, 4 adult male C57B16 mice were injected via their tail vein with 2×80 mg/kg of either: the antimiR sequence or the mismatch ("mm" in FIGS. 5 and 6) sequence using the same chemistry dissolved in saline, and using saline alone ("sal" in FIGS. 5 and 6) as a control (Table 2). Linker 1 in Table 2 corresponds to linker structures (XI) and (XIII) described herein. Linker 2 in Table 2 corresponds to linker structures (X) and (XII) described herein. For comparison, the linker of structure (XIV) was used as a control.

(including the phosphate linkage between the cholesterol linker and oligonucleotide).

TABLE 2

| Polynucleotide | Phosphorothioate (Ps) | Cholesterol | Side of conjugation | Linker |
|---|---|---|---|---|
| antagomiR | Yes | Yes | 3' | Structure (XIV) |
| No PS | No | No | — | — |
| PS | Yes | No | — | — |
| 3' chol linker #1, no PS | No | Yes | 3' | linker #1 |
| 3' chol linker #2, no PS | No | Yes | 3' | linker #2 |
| 5' chol linker #1 | Yes | Yes | 5' | linker #1 |
| 3' chol linker #1 | Yes | Yes | 3' | linker #1 |
| 5' chol linker #2 | Yes | Yes | 5' | linker #2 |
| 3' chol linker #2 | Yes | Yes | 3' | linker #2 |

Three days after the last injection the animals were sacrificed and heart, liver, lungs and kidneys were collected. RNA was extracted from cardiac tissue to determine the effect on cardiac expression of miR-208 by Northern blot analysis (FIG. 5) and quantified using realtime PCR for miR-208 (FIG. 6). These data re-confirm efficient cardiac knockdown using the antagomiR design. However, the absence of either cholesterol or phosphorothioate prohibits the chemistry from establishing significant cardiac knockdown of miR-208 in vivo. Using either the C4 or C6 linker for cholesterol linkage to either the 5' or 3' end of the oligo, indicate that both linkers are suitable for the linkage of cholesterol. Using C6 at the 3' end of the oligo induces an even more efficient knockdown of miR-208 than the original antagomiR against miR-208

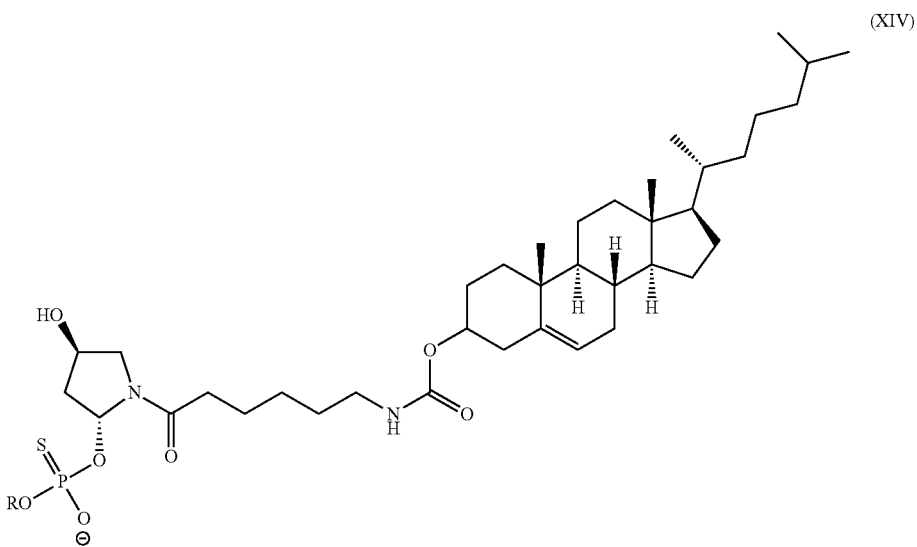

(XIV)

Figure 5:
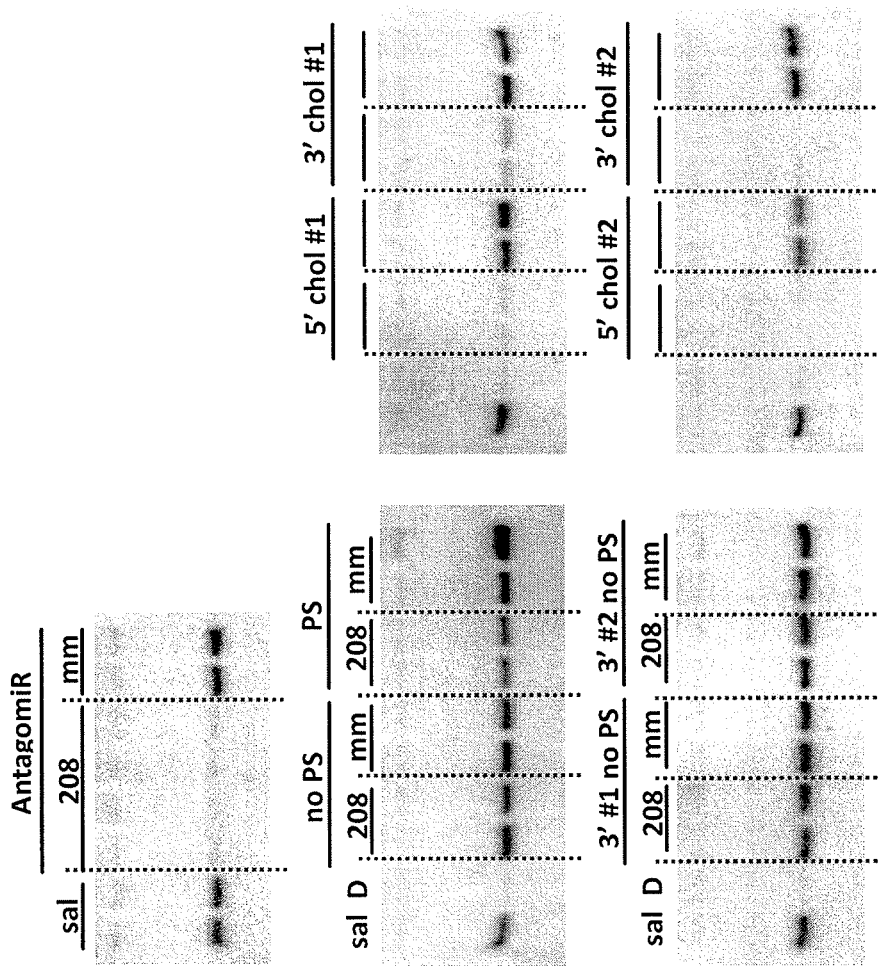
FIG. 5 is a Northern analysis of miR-208 in response to IV injection with the chemistries shown in Table 2.
Figure 6:
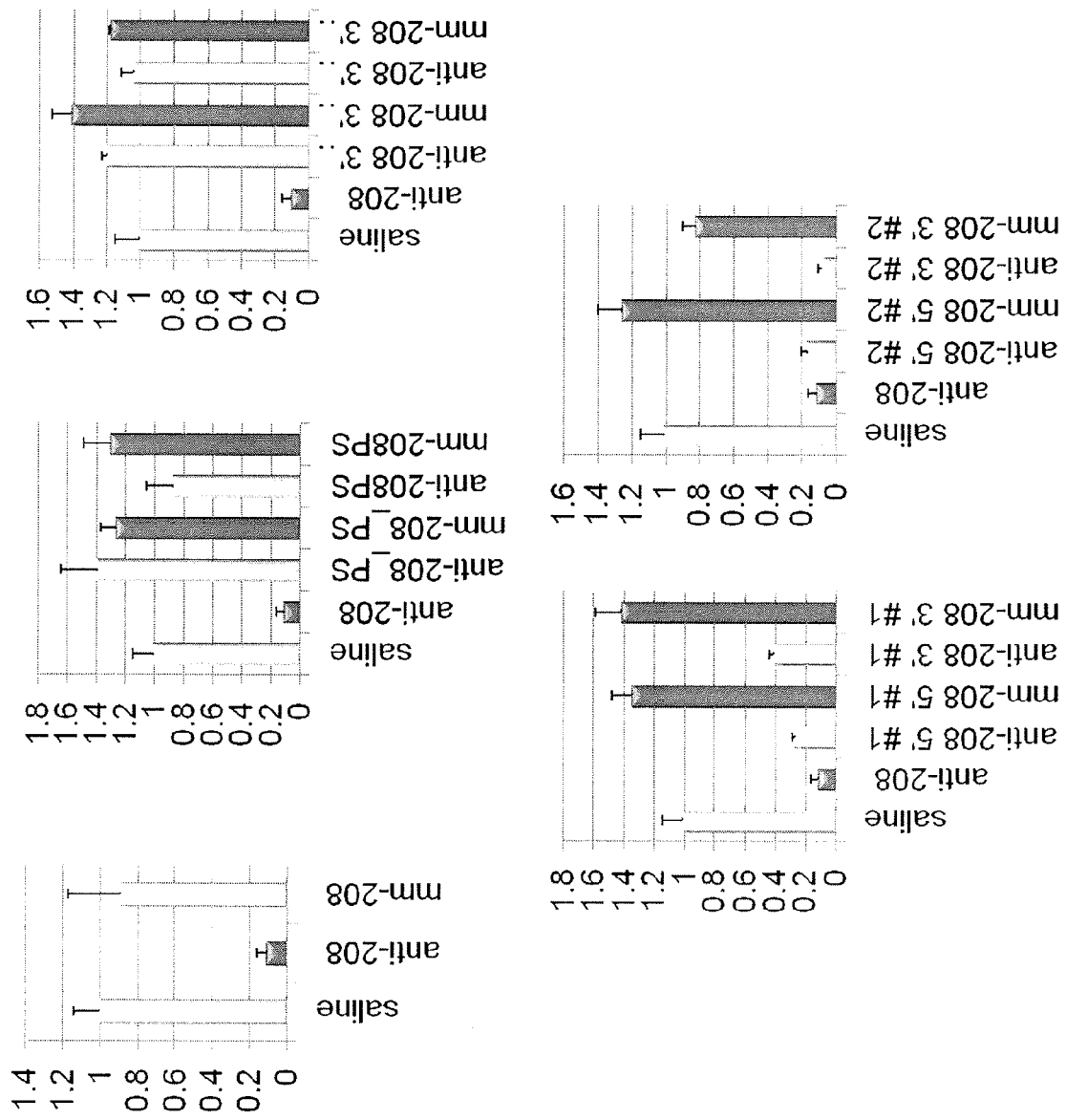
FIG. 6 shows realtime quantification of miR-208 knockdown in response to IV injection with the indicated chemistries compared to saline injected animals.

Further, phosphorothioate (PS) refers to a substitution pattern in which the last two internucleotide bonds on the 5'-end are phosphorothioate linkages, and the first 5 internucleotide phosphate bonds on the 3'-end are phosphorothioate linkages (FIGS. 5 and 6). These data indicate that, unlike the in vitro system, a lipid moiety such as cholesterol and phosphorothioate is desirable for cardiomyocyte knockdown, and both linkers, either 5' or 3', are sufficient in cholesterol linkage to the oligo and are able to establish a comparable if not enhanced knockdown of miR-208 compared to the original antagomiR design. See FIG. 5.

Experimental Protocols

Northern blotting for miRNAS

To assess knockdown of miR-208 in response to the different chemistries and conjugates, Northern blot analysis using a probe directed against miR-208 served to detect the presence of miR-208 in the heart. Using Trizol reagent total RNA is collected from the heart, of which 10 ug is used for Northern blotting. To this end RNA samples are run on 20% acrylamide denaturing gels and transferred to Zeta-probe GT genomic blotting membranes (Bio-Rad) by electrophoresis. After transfer, blots are cross-linked and baked at 80° C. for 1 hr. To maximize the sensitivity of miRNA detection, oligonucleotide probes are labeled with the Starfire Oligos Kit (IDT, Coralville, Iowa) and α-32P dATP (Amersham). Probes are hybridized to the membranes overnight at 39° C. in Rapid-hyb buffer (Amersham), after which they are washed twice for 10 minutes at 39° C. with 0.5×SSC containing 0.1% SDS. The blots are exposed and a U6 probe will serve as a loading control (U6 forward: 5-GTGCTCGCTTCG-GCAGC-3 (SEQ ID NO: 64), U6 reverse: 5-AAAATATG-GAACGCTTCACGAATTTGCG-3 (SEQ ID NO: 65)). The intensity of the radioactive signal will be used to quantify the fold change in expression using a phosphorimager and ImageQuant (Bio-Rad).

Real-time PCR Analysis

In addition to Northern blot analysis we performed miRNA specific realtime PCR analysis to both verify and quantify the level of miR-208 knockdown. Two pg RNA from each tissue sample was used to generate cDNA using Super Script II reverse transcriptase per manufacturer's specifications (Invitrogen Life Technologies Inc., Burlington, Ontario, Canada). Real time PCR is cycled between 95° C./30 s and 60° C./30 for 40 cycles, following an initial denaturation step at 95° C. for 3 min using Taqman probes purchased from ABI. Amplification products are routinely checked using dissociation curve software (Biorad), and transcript quantities are compared using the relative Ct method, where the amount of target normalized to the amount of endogenous SnoRNAs and relative to the control sample is given by $2^{-\Delta\Delta Cr}$.

REFERENCES

Krieg, A. M., Tonkinson, J., Matson, S., Zhao, Q., Saxon, M., Zhang, L. M., Bhanja, U., Yakubov, L., and Stein, C. A. 1993. Modification of antisense phosphodiester oligodeoxynucleotides by a 5'-cholesteryl moiety increases cellular association and improves efficacy. *Proc Natl Acad Sci USA* 90:1048+-1052.

Bijsterbosch, M. K., Manoharan, M., Dorland, R., Waarlo, I. H. E., Biessen, E. A. L., and van Berkel, T. J. C. 2001. Delivery of cholesteryl-conjugated phosphorothioate oligodeoxynucleotides to Kupffer cells by lactosylated low-density lipoprotein. *Biochem Pharmacol* 62:627-633.

Manoharan, M., Tivel, K. L., Condon, T. P., Andrade, L. K., Barber-Peoch, I., Inamati, G., Shah, S., Mohan, V., Graham, M. J., Bennett, C. F., Crooke, S. T., and Cook, P. D. 1997. Conjugated antisense oligonucleotides. *Nucleosides Nucleotides* 16:1129-1138.

Ghosh, Y K, Visweswariah, S S, and Bhattacharya, S. 2002. Advantage of the Ether Linkage between the Positive Charge and the Cholesteryl Skeleton in Cholesterol-Based Amphiphiles as Vectors for Gene Delivery. *Bioconjugate Chem*, 13:378-384.

Ghosh, Y K, Visweswariah, S S, and Bhattacharya, S. 2000. Nature of linkage between the cationic headgroup and cholesteryl skeleton controls gene transfection efficiency. *FEBS Letters*, 473:341-344.

Song, Y K, Liu, F, Chu, S, and Liu, D. 1997. Characterization of Cationic Liposome-Mediated Gene Transfer In Vivo by Intravenous Administration. *Hum Gene Ther*, 8:1585-1592.

The invention claimed is:
1. A lipophilic polynucleotide conjugate, comprising:
  a) a polynucleotide; and
  b) a lipophilic moiety selected from cholesterol, cholestene, cholestane, cholestadiene, bile acid, cholic acid, deoxycholic acid, or dehydrocholic acid,
  wherein the lipophilic moiety is spaced from the polynucleotide and any polar groups or exchangeable protons by a C4 to C10 hydrocarbon linker that is conjugated to the lipophilic moiety through an ether or thioether linkage,
  wherein the hydrocarbon linker separates any polar groups or exchangeable protons from the lipophilic moiety by at least 6 atoms, and
  wherein the hydrocarbon linker is conjugated to the polynucleotide through the polynucleotide 3' position.

2. The conjugate of claim 1, wherein the lipophilic moiety is capable of intercalating with a phospholipid bi-layer.

3. The conjugate of claim 1, wherein the hydrocarbon linker separates any polar groups or exchangeable protons from the lipophilic moiety by 6, 7, 8 or 9 atoms.

4. The conjugate of claim 1, wherein the hydrocarbon linker comprises a C5-C8 cyclic hydrocarbon.

5. The conjugate of claim 1, wherein the hydrocarbon linker is a C4-C8 saturated hydrocarbon, which is optionally substituted.

6. The conjugate of 1, wherein the hydrocarbon linker is conjugated on the end opposite the lipophilic moiety to the polynucleotide.

7. The conjugate of claim 6, wherein the hydrocarbon linker is conjugated to the polynucleotide through a phosphate ester or ether linkage.

8. The conjugate of claim 1, wherein the conjugate has a structure selected from Structures:

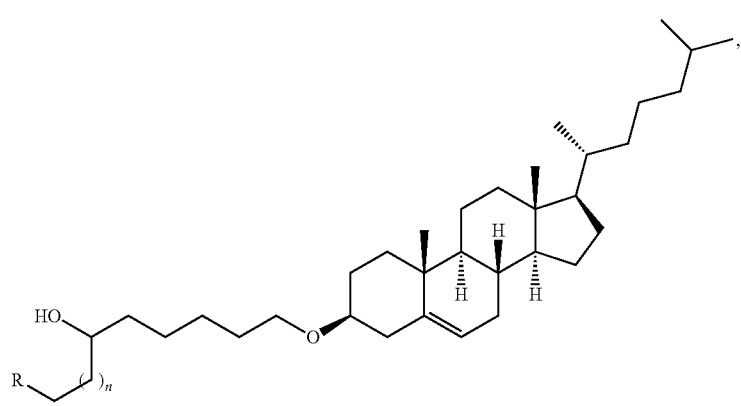

(I)

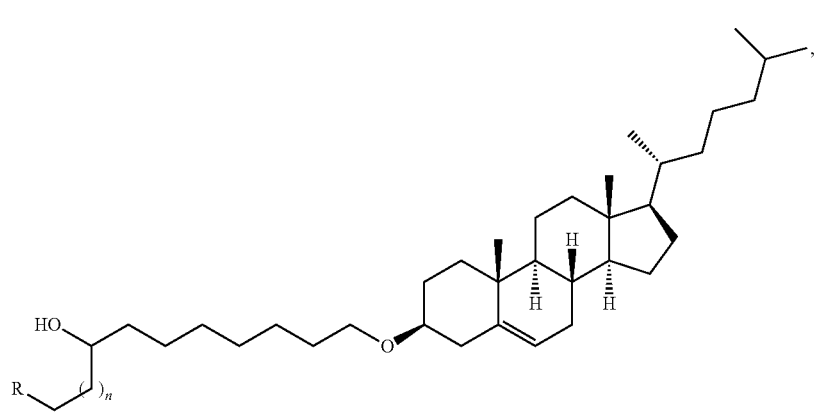

(II)

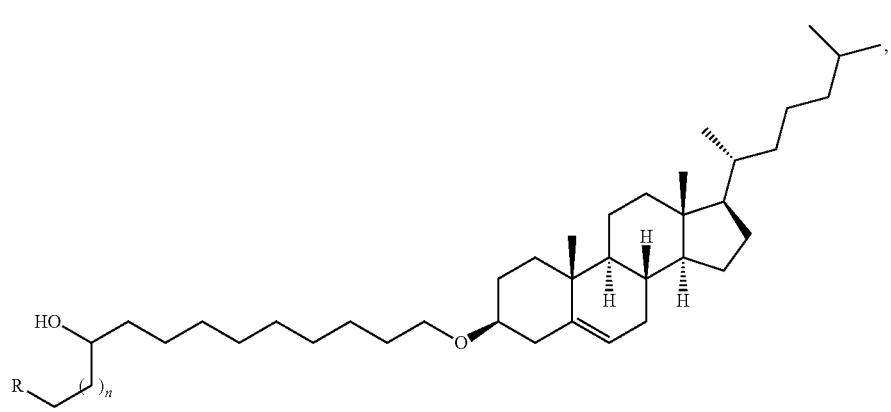

(III)

wherein for Structures (I)-(III), n is 1 or 2, and R is a nucleotide or polynucleotide linked through the 3' position, optionally through a linking group,
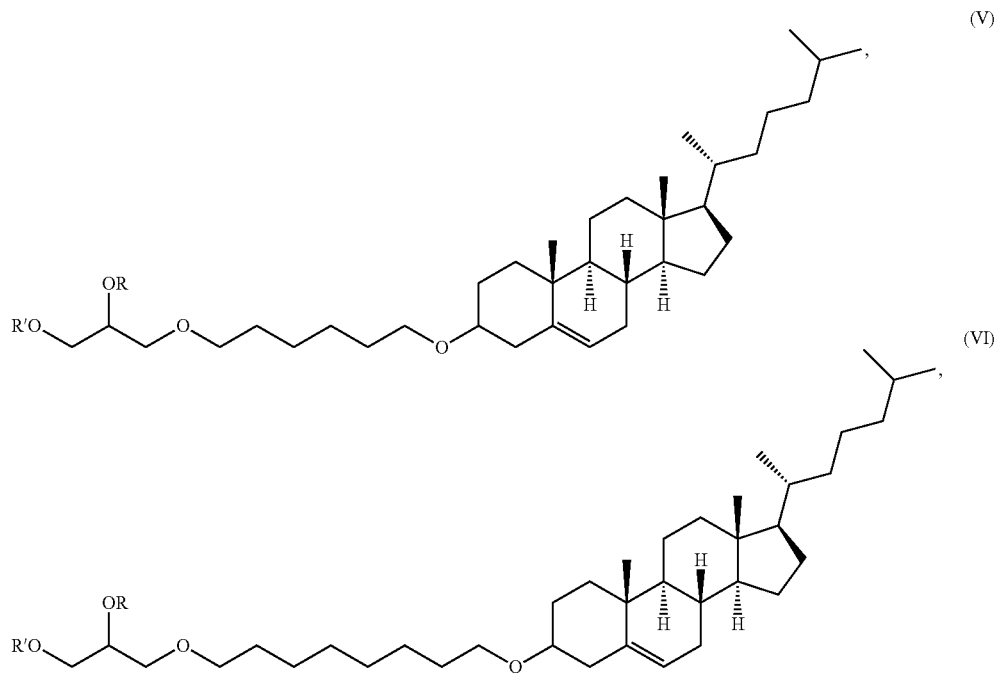
wherein for Structures (V) or (VI), one of R and R' is H and the other is a phosphate polynucleotide,
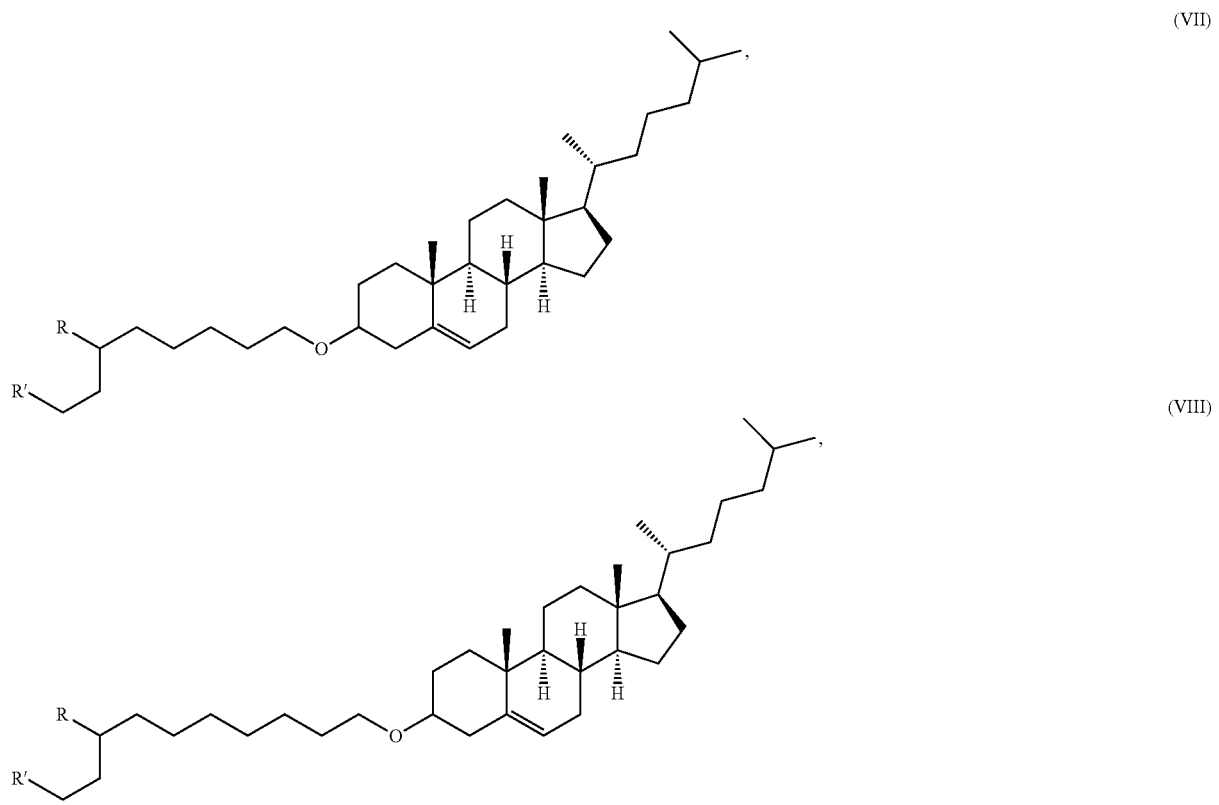

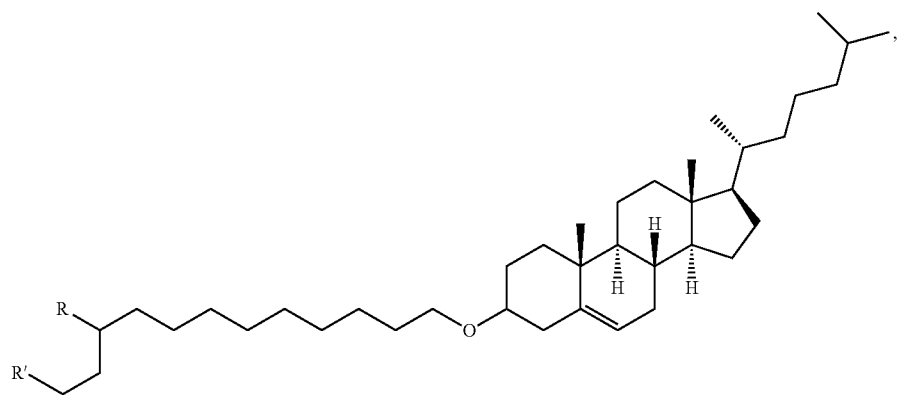
wherein for Structures (VII)-(IX), one of R and R' is H or OH, and the other is a phosphate polynucleotide,
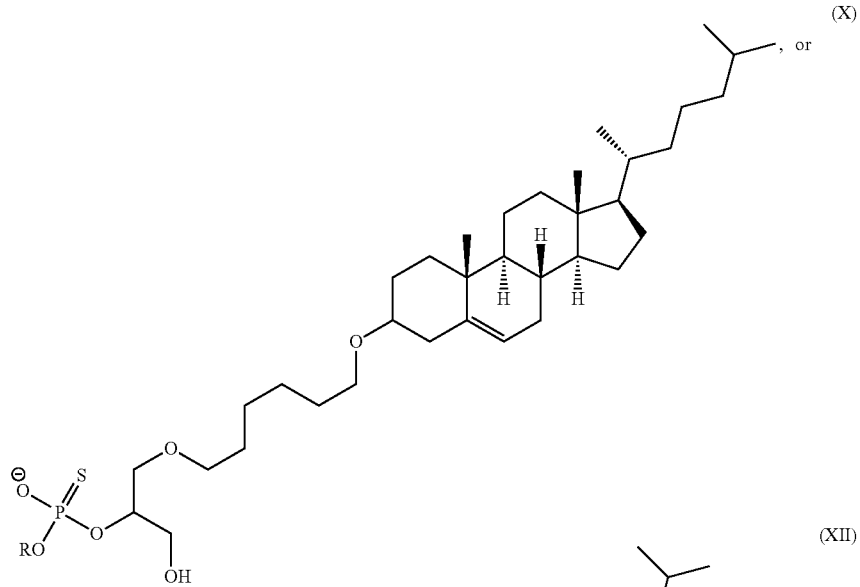
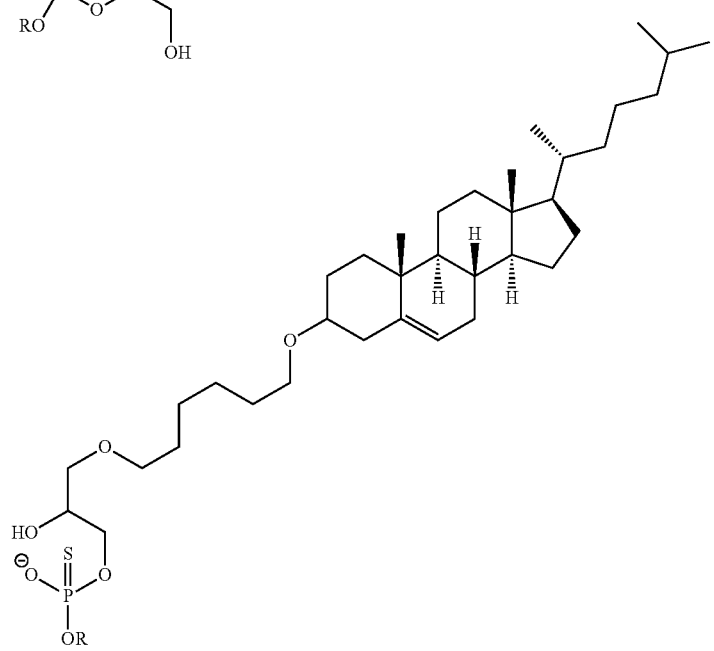

wherein for Structures (X) or (XII), R is a polynucleotide chain.

9. The conjugate of claim 1, wherein the polynucleotide is DNA-based.

10. The conjugate of claim 1, wherein the polynucleotide is RNA-based.

11. The conjugate of claim 1, wherein the polynucleotide has a modified polynucleotide backbone.

12. The conjugate of claim 11, wherein the polynucleotide contains one or more phosphorothioate modifications.

13. The conjugate of claim 1, wherein the polynucleotide has one or more modified nucleoside units.

14. The conjugate of claim 1, wherein the polynucleotide has one or more single stranded and one or more double stranded regions.

15. The conjugate of claim 14, wherein the polynucleotide is an antisense oligonucleotide, short interfering RNA (sRNA), double stranded RNA (dsRNA), single stranded RNA (ssRNA), microRNA (miRNA), short hairpin RNA (shRNA), or ribozyme.

16. The conjugate of claim 15, wherein the polynucleotide is an antagomir.

17. The conjugate of claim 15 or 16, wherein the polynucleotide is about 5 to about 50 nucleotides in length.

18. The conjugate of claim 15 or 16, wherein the polynucleotide is about 18 to about 30 nucleotides in length.

19. The conjugate of claim 15 or 16, wherein the polynucleotide comprises a sequence that is 100% complementary to a mature miRNA.

20. The conjugate of claim 15 or 16, wherein the polynucleotide comprises a sequence that is 100% complementary to a mature miRNA of SEQ ID NO: 1 to 63.

21. The conjugate of claim 15 or 16, wherein the polynucleotide has a sequence designed to mimic a cellular miRNA.

22. The conjugate of claim 15 or 16, wherein the polynucleotide has a sequence designed to mimic a miRNA of SEQ ID NO: 1 to 63.

23. The conjugate of claim 1, wherein the polynucleotide comprises one or more of a locked nucleic acid, peptide nucleic acid backbone, and/or a sugar modification at the 2' or 4' position.

24. A pharmaceutical composition, comprising the conjugate of claim 1 formulated for delivery to a patient.

25. The pharmaceutical composition of claim 24, wherein the conjugate is formulated as a colloidal dispersion system, macromolecular complex, nanocapsule, microsphere, bead, oil-in-water emulsion, micelle, mixed micelle, or liposome.

26. The pharmaceutical composition of claim 25, wherein the conjugate is formulated as a liposome and wherein the lipophilic moiety anchors the polynucleotide conjugate in the liposome.

27. The pharmaceutical composition of any one of claims 24 to claim 26, wherein the composition is formulated for intradermal delivery, subcutaneous delivery, intramuscular delivery, intraperitoneal or intravenous delivery.

28. The pharmaceutical composition of claim 27, wherein the composition is formulated for administration by a cardiac catheter system.

29. A method for delivering a polynucleotide to a mammalian cell, comprising administering the polynucleotide as a conjugate in accordance with claim 1.

30. The method of claim 29, wherein the polynucleotide is a miRNA or a miRNA inhibitor.

31. The method of claim 30, wherein the patient has a condition associated with miRNA expression.

32. The method of claim 31, wherein the condition is one or more of cardiac hypertrophy, myocardial infarction, heart failure, vascular damage, and pathologic cardiac fibrosis.

33. A method for synthesizing a lipophilic polynucleotide conjugate, comprising:
   a) preparing a lipophilic moiety conjugate comprising a lipophilic moiety selected from cholesterol, cholestene, cholestane, cholestadiene, bile acid, cholic acid, deoxycholic acid, or dehydrocholic acid conjugated to a C4 to C10 hydrocarbon linker through an ether or thioether group, the lipophilic moiety conjugate having terminal functional groups to thereby prepare a first intermediate, wherein the lipophilic moiety is spaced from the terminal functional group and any polar groups or exchangeable protons by the hydrocarbon linker;
   b) preparing from said first intermediate, a second intermediate that has functional groups suitable for incorporation into a polynucleotide chain; and
   c) incorporating the second intermediate into a polynucleotide chain during solid phase synthesis,
   wherein the synthesized lipophilic polynucleotide conjugate, formed from said intermediates, has a hydrocarbon linker that separates any polar groups or exchangeable protons from the lipophilic moiety by at least 6 atoms, and
   wherein the hydrocarbon linker is conjugated to the polynucleotide chain through the polynucleotide 3' position.

34. The method of claim 33, wherein the hydrocarbon linker is a C4-C8 alkyl, alkenyl, or alkynyl, and wherein the hydrocarbon is optionally substituted.

35. The method of claim 34, wherein the hydrocarbon linker is a C4-C8 alkyl.

36. The method of claim 33, wherein the first intermediate is reacted to prepare a phosphoramidite as the second intermediate.

37. The method of claim 36, wherein the phosphoramidite is converted to a phosphate ester during solid phase polynucleotide synthesis.

38. The method of claim 33, wherein the first intermediate is reacted to prepare a suitable terminal group for coupling to a support, thereby forming the 3' end of a polynucleotide chain.

39. The method of claim 33, wherein the second intermediate is prepared from a compound having two differentiated hydroxyl groups separated by at least one carbon.

40. A method for synthesizing a polynucleotide conjugate, comprising:
   a) preparing a lipophilic moiety conjugate comprising a lipophilic moiety selected from cholesterol, cholestene, cholestane, cholestadiene, bile acid, cholic acid, deoxycholic acid, or dehydrocholic acid and a C4 to C10 hydrocarbon linker conjugated to the lipophilic moiety through an ether or thioether group, and having terminal functional groups to thereby prepare an intermediate, wherein the lipophilic moiety is spaced from the terminal functional group and any polar groups or exchangeable protons by the hydrocarbon linker; and
   b) coupling the intermediate to the 3' position of a polynucleotide,
   wherein the synthesized polynucleotide conjugate, formed from the intermediate, has a hydrocarbon linker that separates any polar groups or exchangeable protons from the lipophilic moiety by at least 6 atoms.

41. The conjugate of claim 1, wherein the conjugate has the following structure:

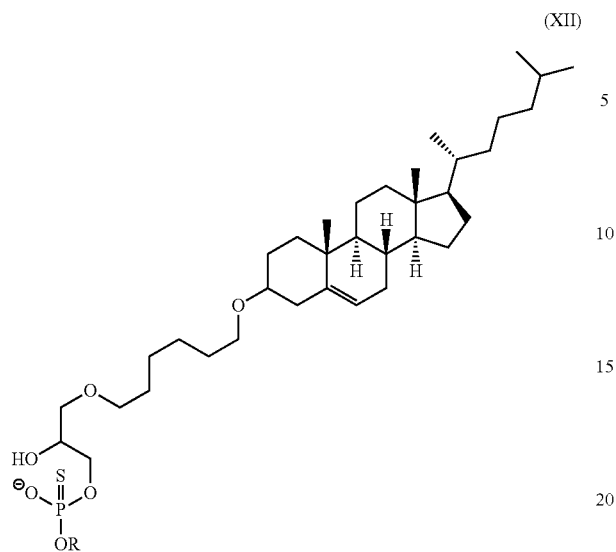

wherein R is a polynucleotide chain.

42. The conjugate of claim 1, wherein the conjugate has the following structure:

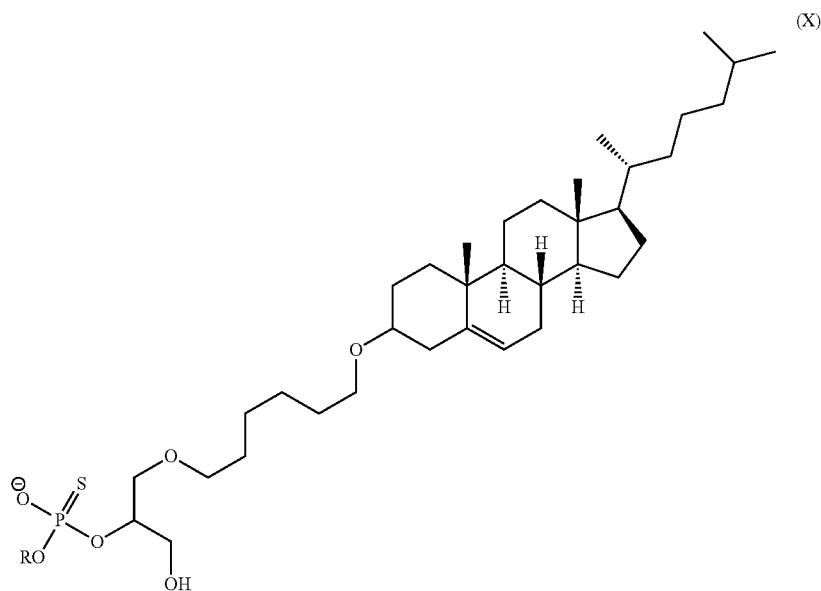

wherein R is a polynucleotide chain.

43. The conjugate of claim 1, wherein the lipophilic moiety is cholesterol.

44. The conjugate of claim 1, wherein the hydrocarbon linker is a $C_6$ alkyl, alkenyl, or alkynyl, and wherein the hydrocarbon is optionally substituted.

45. The method of claim 33, wherein the hydrocarbon linker is a $C_6$ alkyl, alkenyl, or alkynyl, and wherein the hydrocarbon is optionally substituted.

* * * * *

SEQUENCE LISTING

```
<160> NUMBER OF SEQ ID NOS: 65

<210> SEQ ID NO 1
<211> LENGTH: 22
<212> TYPE: RNA
<213> ORGANISM: Homo sapiens

<400> SEQUENCE: 1
uggaauguaa agaaguaugu au                                           22

<210> SEQ ID NO 2
<211> LENGTH: 22
<212> TYPE: RNA
<213> ORGANISM: Homo sapiens

<400> SEQUENCE: 2
aacccguaga uccgaacuug ug                                           22

<210> SEQ ID NO 3
<211> LENGTH: 23
<212> TYPE: RNA
<213> ORGANISM: Homo sapiens

<400> SEQUENCE: 3
```

```
uacccuguag aaccgaauuu gug                                              23

<210> SEQ ID NO 4
<211> LENGTH: 22
<212> TYPE: RNA
<213> ORGANISM: Homo sapiens

<400> SEQUENCE: 4
ucccugagac ccuaacuugu ga                                               22

<210> SEQ ID NO 5
<211> LENGTH: 21
<212> TYPE: RNA
<213> ORGANISM: Homo sapiens

<400> SEQUENCE: 5
ucacagugaa ccggucucuu u                                                21

<210> SEQ ID NO 6
<211> LENGTH: 22
<212> TYPE: RNA
<213> ORGANISM: Homo sapiens

<400> SEQUENCE: 6
uuuggucccc uucaaccagc ug                                               22

<210> SEQ ID NO 7
<211> LENGTH: 22
<212> TYPE: RNA
<213> ORGANISM: Homo sapiens

<400> SEQUENCE: 7
uuuggucccc uucaaccagc ua                                               22

<210> SEQ ID NO 8
<211> LENGTH: 22
<212> TYPE: RNA
<213> ORGANISM: Homo sapiens

<400> SEQUENCE: 8
ucuacagugc acgugucucc ag                                               22

<210> SEQ ID NO 9
<211> LENGTH: 21
<212> TYPE: RNA
<213> ORGANISM: Homo sapiens

<400> SEQUENCE: 9
ugagaugaag cacuguagcu c                                                21

<210> SEQ ID NO 10
<211> LENGTH: 23
<212> TYPE: RNA
<213> ORGANISM: Homo sapiens

<400> SEQUENCE: 10
guccaguuuu cccaggaauc ccu                                              23

<210> SEQ ID NO 11
<211> LENGTH: 22
<212> TYPE: RNA
<213> ORGANISM: Homo sapiens

<400> SEQUENCE: 11
```
ucucccaacc cuuguaccag ug    22

<210> SEQ ID NO 12
<211> LENGTH: 22
<212> TYPE: RNA
<213> ORGANISM: Homo sapiens

<400> SEQUENCE: 12
uagcagcaca uaaugguuug ug    22

<210> SEQ ID NO 13
<211> LENGTH: 22
<212> TYPE: RNA
<213> ORGANISM: Homo sapiens

<400> SEQUENCE: 13
uagcagcaca ucaugguuua ca    22

<210> SEQ ID NO 14
<211> LENGTH: 22
<212> TYPE: RNA
<213> ORGANISM: Homo sapiens

<400> SEQUENCE: 14
uagcagcacg uaaauauugg cg    22

<210> SEQ ID NO 15
<211> LENGTH: 23
<212> TYPE: RNA
<213> ORGANISM: Homo sapiens

<400> SEQUENCE: 15
aacauucauu gcugucggug ggu    23

<210> SEQ ID NO 16
<211> LENGTH: 21
<212> TYPE: RNA
<213> ORGANISM: Homo sapiens

<400> SEQUENCE: 16
uagcagcaca gaaauauugg c    21

<210> SEQ ID NO 17
<211> LENGTH: 22
<212> TYPE: RNA
<213> ORGANISM: Homo sapiens

<400> SEQUENCE: 17
uucaccaccu ucuccaccca gc    22

<210> SEQ ID NO 18
<211> LENGTH: 23
<212> TYPE: RNA
<213> ORGANISM: Homo sapiens

<400> SEQUENCE: 18
cccaguguuc agacuaccug uuc    23

<210> SEQ ID NO 19
<211> LENGTH: 23
<212> TYPE: RNA
<213> ORGANISM: Homo sapiens

```
<400> SEQUENCE: 19
cccaguguuu agacuaucug uuc                                          23

<210> SEQ ID NO 20
<211> LENGTH: 22
<212> TYPE: RNA
<213> ORGANISM: Homo sapiens

<400> SEQUENCE: 20
acaguagucu gcacauuggu ua                                           22

<210> SEQ ID NO 21
<211> LENGTH: 22
<212> TYPE: RNA
<213> ORGANISM: Homo sapiens

<400> SEQUENCE: 21
uggaauguaa ggaagugugu gg                                           22

<210> SEQ ID NO 22
<211> LENGTH: 22
<212> TYPE: RNA
<213> ORGANISM: Homo sapiens

<400> SEQUENCE: 22
auaagacgag caaaaagcuu gu                                           22

<210> SEQ ID NO 23
<211> LENGTH: 22
<212> TYPE: RNA
<213> ORGANISM: Homo sapiens

<400> SEQUENCE: 23
auaagacgaa caaaagguuu gu                                           22

<210> SEQ ID NO 24
<211> LENGTH: 23
<212> TYPE: RNA
<213> ORGANISM: Homo sapiens

<400> SEQUENCE: 24
uaaagugcuu auagugcagg uag                                          23

<210> SEQ ID NO 25
<211> LENGTH: 22
<212> TYPE: RNA
<213> ORGANISM: Homo sapiens

<400> SEQUENCE: 25
uagcuuauca gacugauguu ga                                           22

<210> SEQ ID NO 26
<211> LENGTH: 22
<212> TYPE: RNA
<213> ORGANISM: Homo sapiens

<400> SEQUENCE: 26
acagcaggca cagacaggca gu                                           22

<210> SEQ ID NO 27
<211> LENGTH: 22
<212> TYPE: RNA
<213> ORGANISM: Homo sapiens
```

```
<400> SEQUENCE: 27
aagcugccag uugaagaacu gu                                    22

<210> SEQ ID NO 28
<211> LENGTH: 23
<212> TYPE: RNA
<213> ORGANISM: Homo sapiens

<400> SEQUENCE: 28
agcuacauug ucugcugggu uuc                                   23

<210> SEQ ID NO 29
<211> LENGTH: 21
<212> TYPE: RNA
<213> ORGANISM: Homo sapiens

<400> SEQUENCE: 29
agcuacaucu ggcuacuggg u                                     21

<210> SEQ ID NO 30
<211> LENGTH: 23
<212> TYPE: RNA
<213> ORGANISM: Homo sapiens

<400> SEQUENCE: 30
caagucacua gugguuccgu uua                                   23

<210> SEQ ID NO 31
<211> LENGTH: 21
<212> TYPE: RNA
<213> ORGANISM: Homo sapiens

<400> SEQUENCE: 31
aucacauugc cagggauuuc c                                     21

<210> SEQ ID NO 32
<211> LENGTH: 22
<212> TYPE: RNA
<213> ORGANISM: Homo sapiens

<400> SEQUENCE: 32
uucaaguaau ycaggauagg yu                                    22

<210> SEQ ID NO 33
<211> LENGTH: 21
<212> TYPE: RNA
<213> ORGANISM: Homo sapiens

<400> SEQUENCE: 33
uucaaguaau ucaggauagg u                                     21

<210> SEQ ID NO 34
<211> LENGTH: 22
<212> TYPE: RNA
<213> ORGANISM: Homo sapiens

<400> SEQUENCE: 34
aaggagcuca cagucuauug ag                                    22

<210> SEQ ID NO 35
<211> LENGTH: 22
<212> TYPE: RNA
```

<213> ORGANISM: Homo sapiens

<400> SEQUENCE: 35
uagcaccauc ugaaaucggu ua        22

<210> SEQ ID NO 36
<211> LENGTH: 23
<212> TYPE: RNA
<213> ORGANISM: Homo sapiens

<400> SEQUENCE: 36
uagcaccauu ugaaaucagu guu       23

<210> SEQ ID NO 37
<211> LENGTH: 22
<212> TYPE: RNA
<213> ORGANISM: Homo sapiens

<400> SEQUENCE: 37
uagcaccauu ugaaaucggu ua        22

<210> SEQ ID NO 38
<211> LENGTH: 22
<212> TYPE: RNA
<213> ORGANISM: Homo sapiens

<400> SEQUENCE: 38
uguaaacauc cucgacugga ag        22

<210> SEQ ID NO 39
<211> LENGTH: 22
<212> TYPE: RNA
<213> ORGANISM: Homo sapiens

<400> SEQUENCE: 39
uguaaacauc cuacacucag cu        22

<210> SEQ ID NO 40
<211> LENGTH: 23
<212> TYPE: RNA
<213> ORGANISM: Homo sapiens

<400> SEQUENCE: 40
uguaaacauc cuacacucuc agc       23

<210> SEQ ID NO 41
<211> LENGTH: 22
<212> TYPE: RNA
<213> ORGANISM: Homo sapiens

<400> SEQUENCE: 41
uguaaacauc cccgacugga ag        22

<210> SEQ ID NO 42
<211> LENGTH: 22
<212> TYPE: RNA
<213> ORGANISM: Homo sapiens

<400> SEQUENCE: 42
uguaaacauc cuugacugga ag        22

<210> SEQ ID NO 43
<211> LENGTH: 24

```
<212> TYPE: RNA
<213> ORGANISM: Homo sapiens

<400> SEQUENCE: 43
ucucacacag aaaucgcacc cguc                                          24

<210> SEQ ID NO 44
<211> LENGTH: 22
<212> TYPE: RNA
<213> ORGANISM: Homo sapiens

<400> SEQUENCE: 44
gaaguuguuc gugguggauu cg                                            22

<210> SEQ ID NO 45
<211> LENGTH: 22
<212> TYPE: RNA
<213> ORGANISM: Homo sapiens

<400> SEQUENCE: 45
acuggacuua gggucagaag gc                                            22

<210> SEQ ID NO 46
<211> LENGTH: 21
<212> TYPE: RNA
<213> ORGANISM: Homo sapiens

<400> SEQUENCE: 46
acuggacuug gagucagaag g                                             21

<210> SEQ ID NO 47
<211> LENGTH: 22
<212> TYPE: RNA
<213> ORGANISM: Homo sapiens

<400> SEQUENCE: 47
cagcagcaau ucauguuuug aa                                            22

<210> SEQ ID NO 48
<211> LENGTH: 23
<212> TYPE: RNA
<213> ORGANISM: Homo sapiens

<400> SEQUENCE: 48
ucacuccucu ccucccgucu ucu                                           23

<210> SEQ ID NO 49
<211> LENGTH: 22
<212> TYPE: RNA
<213> ORGANISM: Homo sapiens

<400> SEQUENCE: 49
ucaggcucag uccccucccg au                                            22

<210> SEQ ID NO 50
<211> LENGTH: 22
<212> TYPE: RNA
<213> ORGANISM: Homo sapiens

<400> SEQUENCE: 50
uccuguacug agcugccccg ag                                            22

<210> SEQ ID NO 51
```

```
<211> LENGTH: 21
<212> TYPE: RNA
<213> ORGANISM: Homo sapiens

<400> SEQUENCE: 51
cagcagcaca cugugguuug u                                              21

<210> SEQ ID NO 52
<211> LENGTH: 21
<212> TYPE: RNA
<213> ORGANISM: Homo sapiens

<400> SEQUENCE: 52
uuaagacuug cagugauguu u                                              21

<210> SEQ ID NO 53
<211> LENGTH: 23
<212> TYPE: RNA
<213> ORGANISM: Homo sapiens

<400> SEQUENCE: 53
ucggggauca ucaugucacg aga                                            23

<210> SEQ ID NO 54
<211> LENGTH: 22
<212> TYPE: RNA
<213> ORGANISM: Homo sapiens

<400> SEQUENCE: 54
uauugcacuu gucccggccu gu                                             22

<210> SEQ ID NO 55
<211> LENGTH: 22
<212> TYPE: RNA
<213> ORGANISM: Homo sapiens

<400> SEQUENCE: 55
uauugcacuc gucccggccu cc                                             22

<210> SEQ ID NO 56
<211> LENGTH: 22
<212> TYPE: RNA
<213> ORGANISM: Homo sapiens

<400> SEQUENCE: 56
ugagguagua gguuguauag uu                                             22

<210> SEQ ID NO 57
<211> LENGTH: 22
<212> TYPE: RNA
<213> ORGANISM: Homo sapiens

<400> SEQUENCE: 57
ugagguagua gguugugugg uu                                             22

<210> SEQ ID NO 58
<211> LENGTH: 22
<212> TYPE: RNA
<213> ORGANISM: Homo sapiens

<400> SEQUENCE: 58
ugagguagua gguuguaugg uu                                             22
```

-continued

```
<210> SEQ ID NO 59
<211> LENGTH: 22
<212> TYPE: RNA
<213> ORGANISM: Homo sapiens

<400> SEQUENCE: 59
agagguagua gguugcauag uu                                                  22

<210> SEQ ID NO 60
<211> LENGTH: 22
<212> TYPE: RNA
<213> ORGANISM: Homo sapiens

<400> SEQUENCE: 60
ugagguagga gguuguauag uu                                                  22

<210> SEQ ID NO 61
<211> LENGTH: 22
<212> TYPE: RNA
<213> ORGANISM: Homo sapiens

<400> SEQUENCE: 61
ugagguagua gauuguauag uu                                                  22

<210> SEQ ID NO 62
<211> LENGTH: 22
<212> TYPE: RNA
<213> ORGANISM: Homo sapiens

<400> SEQUENCE: 62
ugagguagua guuuguacag uu                                                  22

<210> SEQ ID NO 63
<211> LENGTH: 22
<212> TYPE: RNA
<213> ORGANISM: Homo sapiens

<400> SEQUENCE: 63
aaaccguuac cauuacugag uu                                                  22

<210> SEQ ID NO 64
<211> LENGTH: 17
<212> TYPE: DNA
<213> ORGANISM: Homo sapiens

<400> SEQUENCE: 64
gtgctcgctt cggcagc                                                        17

<210> SEQ ID NO 65
<211> LENGTH: 28
<212> TYPE: DNA
<213> ORGANISM: Homo sapiens

<400> SEQUENCE: 65
aaaatatgga acgcttcacg aatttgcg                                            28
```